United States Patent
Illes et al.

(10) Patent No.: US 8,885,899 B2
(45) Date of Patent: Nov. 11, 2014

(54) METHOD AND A SYSTEM FOR MULTI-DIMENSIONAL VISUALIZATION OF THE SPINAL COLUMN BY VERTEBRA VECTORS, SACRUM VECTOR, SACRUM PLATEAU VECTOR AND PELVIS VECTOR

(75) Inventors: Tamäs Illes, Pécs (HU); Szabolcs Somoskeöy, Pécs (HU)

(73) Assignee: Pécsi Tudományegyetem, Pécs (HU)

(*) Notice: Subject to any disclaimer, the term of this patent is extended or adjusted under 35 U.S.C. 154(b) by 253 days.

(21) Appl. No.: 13/575,970

(22) PCT Filed: Jan. 28, 2011

(86) PCT No.: PCT/HU2011/000013
§ 371 (c)(1),
(2), (4) Date: Feb. 25, 2013

(87) PCT Pub. No.: WO2011/092531
PCT Pub. Date: Aug. 4, 2011

(65) Prior Publication Data
US 2013/0202179 A1    Aug. 8, 2013

Related U.S. Application Data

(60) Provisional application No. 61/298,963, filed on Jan. 28, 2010.

(51) Int. Cl.
*G06K 9/00*   (2006.01)
*G06T 7/60*   (2006.01)
*G06T 17/00*  (2006.01)
*A61B 5/107*  (2006.01)

(52) U.S. Cl.
CPC ....... *G06T 17/00* (2013.01); *G06T 2207/30012* (2013.01); *G06T 7/60* (2013.01); *A61B 5/1075* (2013.01)

USPC .......................................................... 382/128

(58) Field of Classification Search
None
See application file for complete search history.

(56) References Cited

U.S. PATENT DOCUMENTS

| 5,088,504 A     | * | 2/1992 | Benesh et al.    | 600/594 |
| 2002/0138022 A1 | * | 9/2002 | Benesh           | 600/587 |
| 2005/0119593 A1 | * | 6/2005 | Gallard et al.   | 600/594 |
| 2009/0226055 A1 | * | 9/2009 | Dankowicz et al. | 382/128 |

FOREIGN PATENT DOCUMENTS

WO   WO 2007038510 A1 *  4/2007  ............. A61B 17/70

* cited by examiner

*Primary Examiner* — Hadi Akhavannik

(57) ABSTRACT

A new system and method introducing vertebra vectors for the three-dimensional (3D) visualization and its use for the complete 3D characterization and numerical analysis of vertebrae in spinal deformities is covered in this application. A vertebra vector representing its respective vertebra means a simplification of the very complex visual information in digital images and 3D reconstructions provided by the current radiodiagnostic devices, without sacrificing relevant data for the information important to understand the underlying processes in spinal deformation: 3D mathematical data on vertebral size, position, orientation and rotation. A series of vertebra vectors of the thoracic and lumbar spinal region provide the ability of a virtual 3D reconstruction of the spine, in frontal, sagittal and horizontal plane. Conventional angulation measurement methods to describe and characterize the spinal column in the frontal and sagittal plane are preserved and readily applicable by methods using vertebra vectors as well.

4 Claims, 28 Drawing Sheets

Table 1.

| vert | A(A$_x$; A$_y$; A$_z$) | B(B$_x$; B$_y$; B$_z$) | AB(X; Y; Z) | α (°) | ω (°) | αx (°) |
|---|---|---|---|---|---|---|
| T$_1$ | (-24.35; 62.42; 646.84) | (-23.34; 43.02; 639.80) | (1.01; -19.40; -7.04) | -8.16 | 19.95 | -2.98 |
| T$_2$ | (-23.20; 73.34; 624.57) | (-19.18; 48.63; 618.54) | (4.02; -24.71; -6.03) | -33.69 | 13.71 | -9.24 |
| T$_3$ | (-22.34; 79.81; 596.99) | (-21.19; 50.64; 593.83) | (1.15; -29.17; -3.16) | -20.09 | 6.18 | -2.26 |
| T$_4$ | (-26.22; 80.67; 573.41) | (-23.20; 49.78; 573.71) | (3.02; -30.89; 2.30) | 52.71 | -4.26 | -5.58 |
| T$_5$ | (-32.25; 79.09; 548.28) | (-28.66; 45.61; 554.31) | (3.59; -33.48; 6.03) | 30.77 | -10.21 | -6.12 |
| T$_6$ | (-41.31; 71.76; 524.57) | (-42.17; 38.28; 537.64) | (-0.86; -33.48; 13.07) | -3.76 | -21.32 | 1.47 |
| T$_7$ | (-50.79; 61.42; 498.57) | (-53.81; 27.80; 512.22) | (-3.02; -33.62; 13.65) | -72.48 | -22.10 | 5.13 |
| T$_8$ | (-59.70; 53.66; 475.00) | (-61.42; 13.72; 491.38) | (-1.72; -39.94; 16.38) | -5.99 | -22.30 | 2.47 |
| T$_9$ | (-65.30; 43.31; 449.43) | (-71.33; 3.65; 459.49) | (-6.03; -39.66; 10.06) | -30.94 | -14.23 | 8.65 |
| T$_{10}$ | (-68.89; 31.68; 422.42) | (-80.10; -4.53; 435.21) | (-11.21; -36.21; 12.79) | -41.23 | -19.45 | 17.20 |
| T$_{11}$ | (-65.73; 25.07; 391.66) | (-76.22; -12.47; 394.40) | (-10.49; -37.50; 2.44) | -76.91 | -3.72 | 15.63 |
| T$_{12}$ | (-59.27; 21.78; 362.07) | (-64.44; -17.46; 366.96) | (-5.17; -39.22; 4.89) | -46.59 | -7.11 | 7.51 |
| L$_1$ | (-43.60; 16.59; 329.03) | (-50.07; -22.20; 330.90) | (-6.47; -38.79; 1.87) | -73.88 | -2.76 | 9.47 |
| L$_2$ | (-25.21; 9.69; 295.55) | (-27.65; -29.10; 298.85) | (-2.44; -38.79; 3.30) | -36.48 | -4.86 | 3.60 |
| L$_3$ | (-7.54; 7.39; 258.09) | (-3.80; -33.13; 259.20) | (3.74; -40.52; 1.13) | 72.91 | -1.63 | -5.37 |
| L$_4$ | (8.41; 8.54; 218.24) | (12.00; -29.68; 204.60) | (3.59; -38.22; -11.64) | -17.14 | 16.94 | -5.37 |
| L$_5$ | (11.14; 12.57; 173.13) | (11.57; -18.46; 161.06) | (0.43; -31.03; -12.07) | -2.04 | 21.25 | -0.79 |

FIG. 14

Table 2A.

| vert | PCR(PCR$_x$; PCR$_y$; PCR$_z$) | PCL(PCL$_x$; PCL$_y$; PCL$_z$) | IP(X; Y; Z) | θ$_{IP}$ (°) | θ$_S$ (°) |
|---|---|---|---|---|---|
| T$_1$ | (-42.76; 62.34; 646.69) | (-6.34; 62.72; 646.09) | (36.42; 0.37; -0.55) | -0.84 | 19.95 |
| T$_2$ | (-38.87; 71.24; 624.45) | (-7.37; 75.84; 623.7) | (31.49; 4.59; -0.74) | -1.36 | 13.71 |
| T$_3$ | (-36.99; 77.75; 597.85) | (-8.04; 82.06; 595.26) | (28.55; 4.31; -2.58) | -5.18 | 0.18 |
| T$_4$ | (-39.98; 78.86; 574.75) | (-11.52; 83.2; 567.14) | (28.46; 4.03; -7.6) | -14.97 | -4.26 |
| T$_5$ | (-45.9; 76.18; 552.77) | (-18.8; 82; 543.06) | (27.1; 5.82; -9.7) | -19.70 | -10.21 |
| T$_6$ | (-54.57; 70.54; 527.95) | (-27.42; 73.38; 520.76) | (27.15; 2.83; -7.19) | -14.83 | -21.32 |
| T$_7$ | (-62.78; 61.60; 503.41) | (-37.81; 61.26; 492.59) | (24.97; -0.36; -10.81) | -23.42 | -22.10 |
| T$_8$ | (-72.27; 54.42; 478.57) | (-46.89; 53.01; 470.69) | (25.38; -1.41; -7.88) | -17.25 | -22.30 |
| T$_9$ | (-79.08; 45.14; 449.35) | (-52.63; 41.22; 448.52) | (25.45; -3.41; -0.82) | -1.85 | -14.23 |
| T$_{10}$ | (-82.72; 36.15; 421.01) | (-54.47; 27.57; 423.5) | (28.25; -8.57; 2.49) | 5.04 | -19.45 |
| T$_{11}$ | (-81.06; 28.17; 388.86) | (-50.54; 21.09; 394.01) | (30.51; -7.07; 5.14) | 9.57 | -3.72 |
| T$_{12}$ | (-75.55; 24.73; 353.55) | (-41.8; 18.46; 367.19) | (33.74; -6.26; 13.63) | 22.00 | -7.11 |
| L$_1$ | (-58.04; 16.06; 322.15) | (-29.06; 16.5; 336.45) | (28.97; -0.13; 14.29) | 26.26 | -2.76 |
| L$_2$ | (-41.01; 8.9; 287.16) | (-9.73; 10.47; 302.82) | (31.27; 1.56; 15.66) | 26.60 | -4.86 |
| L$_3$ | (-24.31; 5.49; 252.18) | (9.06; 9.07; 263.54) | (33.27; 3.58; 11.36) | 18.85 | -1.63 |
| L$_4$ | (-13.36; 7.45; 213.91) | (30.04; 10.06; 220.03) | (43.4; 2.6; 6.11) | 8.02 | 16.04 |
| L$_5$ | (-33.93; 11.13; 172.15) | (35.45; 15.88; 173.42) | (49.38; 4.75; 1.27) | 1.48 | 21.25 |

FIG. 15

| Table 2B. | |
|---|---|
| T7-L5 Cobb's angle (°) | 50.02 |
| T4-T12 kyphosis (°) | 2.85 |
| L1-L5 lordosis (°) | 24.01 |

FIG. 16

METHOD AND A SYSTEM FOR MULTI-DIMENSIONAL VISUALIZATION OF THE SPINAL COLUMN BY VERTEBRA VECTORS, SACRUM VECTOR, SACRUM PLATEAU VECTOR AND PELVIS VECTOR

This application claims priority to U.S. Provisional Patent Application Ser. No. 61/298,963 filed Jan. 28, 2010, the content of which is hereby incorporated by reference in its entirety into this disclosure.

BACKGROUND

1. Field

The present invention relates generally to a method and a system for multi-dimensional visualization of the spinal column, and more specifically to techniques for 3D visualization of the spinal column comprising vertebral size, position, orientation and rotation and their utilization for description, characterization and quantitative parametric analysis of spinal deformities in frontal, sagittal and horizontal plane.

2. Background

Scoliosis is the most prevalent three-dimensional (3D) spinal deformity affecting about 1% of adolescent population. Diagnosis and classification of scoliotic deformities is almost exclusively based upon frontal and lateral X-ray images. Current classification of adolescent scoliosis has been proposed to be comprehensive and all-inclusive for every curve types but in addition to classifying frontal spinal deviations it only considers sagittal spinal alignment, and ignores axial vertebral rotation [1] that is thought to be an inherent characteristics of scoliotic 3D deformities presented in horizontal plane. The demand for an accurate evaluation of vertebral rotation in scoliosis is hardly new. Biplanar X-ray images provide inadequate quantitative or qualitative information on the anatomical landmarks needed to determine the axial rotation [6,21]. Several measurement methods have been published [2-5], all based on assessment of the relative positions of various posterior vertebral elements. Perdriolle torsiometry [3,4] is currently the most accepted measurement method in clinical practice, but its reproducibility is very limited and cannot be quantified precisely [6,7].

Horizontal plane deviations of the spine are most accurately assessable by computed tomography, but routine use of this diagnostic method is limited due to its relatively high cost and prohibitively high radiation dose [8,9]. Expert opinion is divided on the veracity and reproducibility of CT scans for such measurements [10,11].

The latest classification proposal introduced the concept of the plane of maximum curvature (PMC) and visualization of the PMC through the daVinci representation, which is thought to make the 3D evaluation of scoliosis readily available for routine clinical practice [13].

U.S. Pat. No. 5,582,186 discloses measurement principles and bar plot representation of measured values of the absolute axial rotation and relative intervertebral rotation of individual vertebrae. They perform the measurement of vertebra rotation based on a formerly published indirect method determining the center of the body of vertebra and calculating the relative position of this center point inside the contour lines of the body of vertebra. The method itself is indirect, because the rotation in the horizontal plane is calculated based on anatomical reference points visible in the frontal plane where the accuracy of determination and reproducibility is inadequate, thus reliability of the presented method is low. In addition to vertebral rotation, other three-dimensional properties of the vertebrae (e.g. 3D-position, frontal and sagittal rotation) remain undetermined; the method is not capable for proper 3D characterization of the vertebral column.

US20070073194 describes a method dedicated exclusively for measuring the axial rotation of vertebrae. This solution is based on the principle described by Pedriolle et al. (also cited in our PPA reference list). The horizontal symmetry axis of vertebrae is given by a line defined by the center point of the vertebral body and the end of spinous process. The extent of rotation is estimated by a relative positional change of the ovoid patterns representing the frontal projection of vertebral pedicles. Summarized, this method also determines the extent of axial rotation indirectly. The accuracy and reproducibility has been found to be weak and reliability is considered to be low. In addition to vertebral rotation, other three-dimensional properties of the vertebrae (e.g. 3D-position, frontal and sagittal rotation) remain undetermined; the method is not capable for proper 3D characterization of the vertebral column.

The method known from US20090202122 has been elaborated for determining the centre line of the vertebral column (which surrounds the spinal chord) in the frontal and mainly in the sagittal plane. On axial (or sagittal) tomographic images (e.g. computed tomography) the valid center points for every slice are determined with the help of the posterior vertebral arches and the frontal and rear endpoints of the vertebral foramen; from the series of centre points derived from consecutive slices the position and direction can be represented. Some common feature with the basis of the theory of vertebra vector might be discovered because the origin of the vertebra vector is positioned around the area of the vertebral foramen but is not identical with the centre point of those. Considering that it only represents a spatial alignment of series of points in form of a simple line; it is only capable of defining a three-dimensional position of series of points. It contains no information on the body of vertebrae themselves which lie in front of the vertebral foramen and is unable to provide spatial information and measurement data on rotation and size of those.

US20090226055 describes a method using the fundamental principle of three-dimensional characterization and classification of vertebral column by presenting the plane of maximum curvature, PMC with daVinci representation for scoliotic vertebrae, which is currently being advocated by Scoliosis Research Society as a superior solution to the problems of 3D visualization and characterization of the spine. PMC is a derivative plane defined by 3 centroids of the vertebral bodies determining the scoliotic curve and its horizontal projection is displayed in a Da Vinci graph to be characterized numerically. The very aim for introduction of this method was to provide an assessment for the horizontal plane spinal deviations, namely, axial vertebral rotation. This new method has been available as a new recommendation for two years, but it did not reach a great success with clinicians because it may be too much as an abstraction and too difficult to be comprehended and a little complicated to be presented based on stereographic X-ray images. It is an indirect and incomplete method, is bound to the determination of an invisible, hardly imaginable and complicated 3D plane which falls outside of the vertebral column. For a truly complete 3D characterization of the spinal column, it requires additional data of frontal and sagittal plane spine deviations determined by independent methods. Its relation to the known measurement methods has not been proven yet.

A new low-dose digital radioimaging device based on a Nobel Prize winning X-ray detection technology creates spatially calibrated, simultaneously captured frontal and lateral X-ray images in a standing position of the whole body, available and approved for clinical practice [14,15,16,17]. A special semiautomatic 3D reconstruction software, based on these biplanar calibrated radiographs generates accurate and realistic surface 3D model of thoracic and lumbar vertebrae and the pelvis, complemented with 3D parametric values of frontal and sagittal spinal curves, vertebral orientation and rotation in all 3 planes and sagittal pelvic parameters [18,19]. From representations of planar projections of surface 3D reconstructions, visualization of the spinal geometry in horizontal view has become a routine daily task in scoliosis surgery.

Nevertheless, precise 3D reconstructions from current radiodiagnostic devices provide a very complex visual information that contains way too much data to be computed and extracted, in order to simply characterize and numerically describe spinal deformations, especially in the horizontal plane.

Due to the lack of a definitive and reproducible measurement method in horizontal plane and a need for a simplified yet all-inclusive presentation of the spinal column based on 3D reconstruction images of current radiodiagnostic methods, a new method and system of vertebra vectors is introduced that is capable of the complete visualization, characterization and numerical description of spinal deformities in all 3 planes while preserving conventional methods for the measurement of frontal and sagittal plane curvature of the spine.

SUMMARY

A first object of the invention is to provide a method and a system for multi-dimensional visualization of the spinal column, together with the pelvis. A second object of the invention is to provide a method for provide a reference point for proper positioning of a three-dimensional coordinate system used for visualisation of the spinal column, including the pelvis.

In accordance with the present invention, a method of visulaisation are provided. Embodiments of the invention are claimed in the dependent claims.

BRIEF DESCRIPTION OF THE DRAWINGS

The features, nature, and advantages of the present invention may become more apparent from the detailed description set forth below when taken in conjunction with the drawings in which like reference characters identify correspondingly throughout and wherein.

Figure 5A:
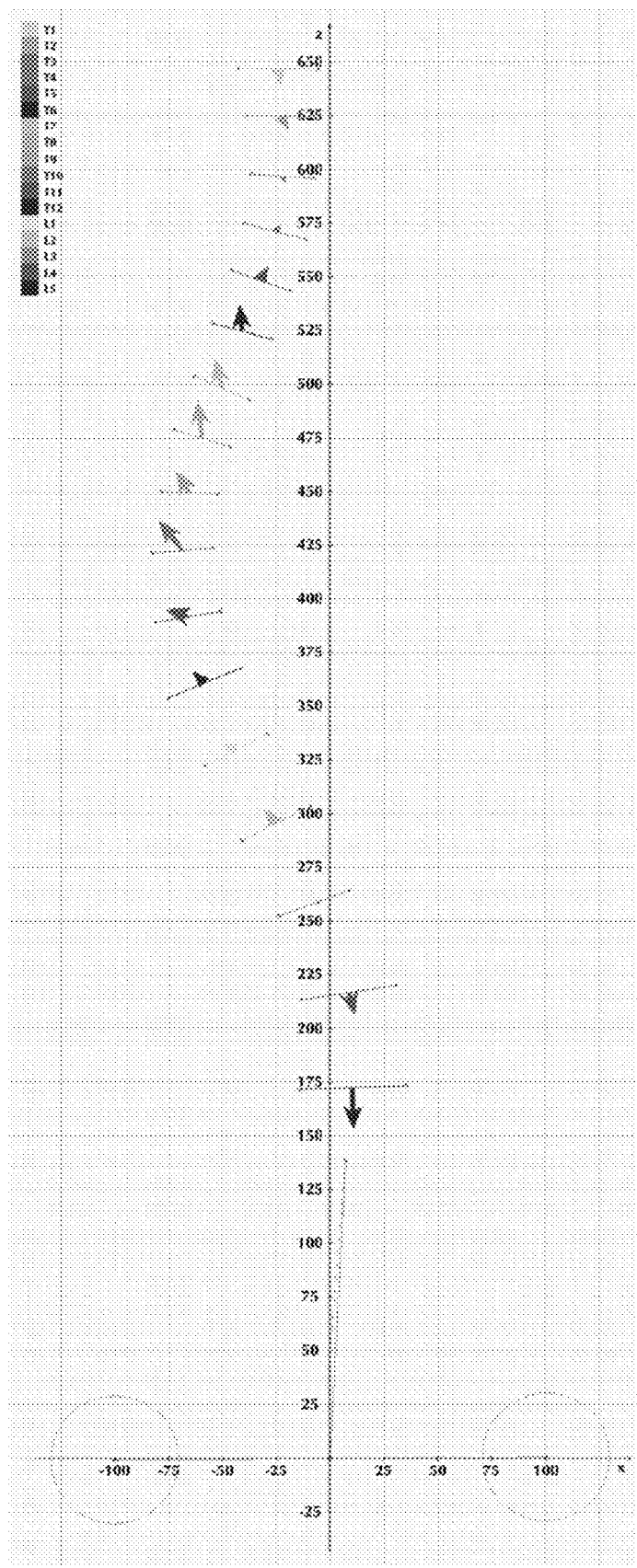
FIGS. 5A-C show visualizations of vertebra vectors of the thoracic and lumbar spinal region for a scoliotic spine in the frontal, sagittal and horizontal plane.
Figure 5B:
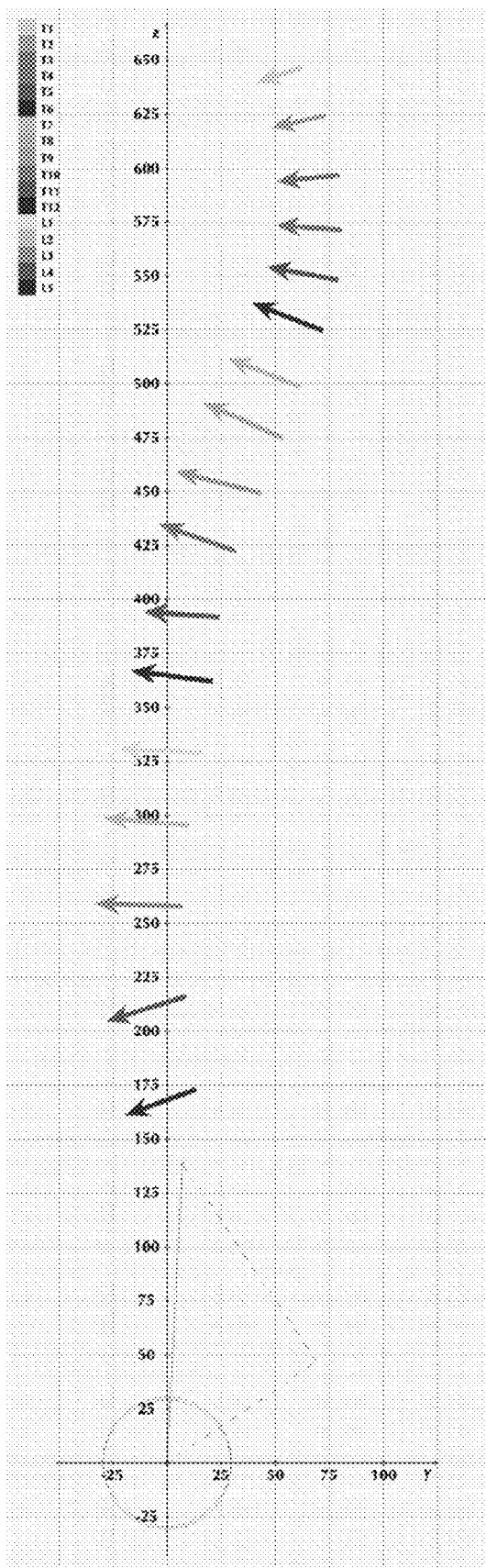
Figure 5C:
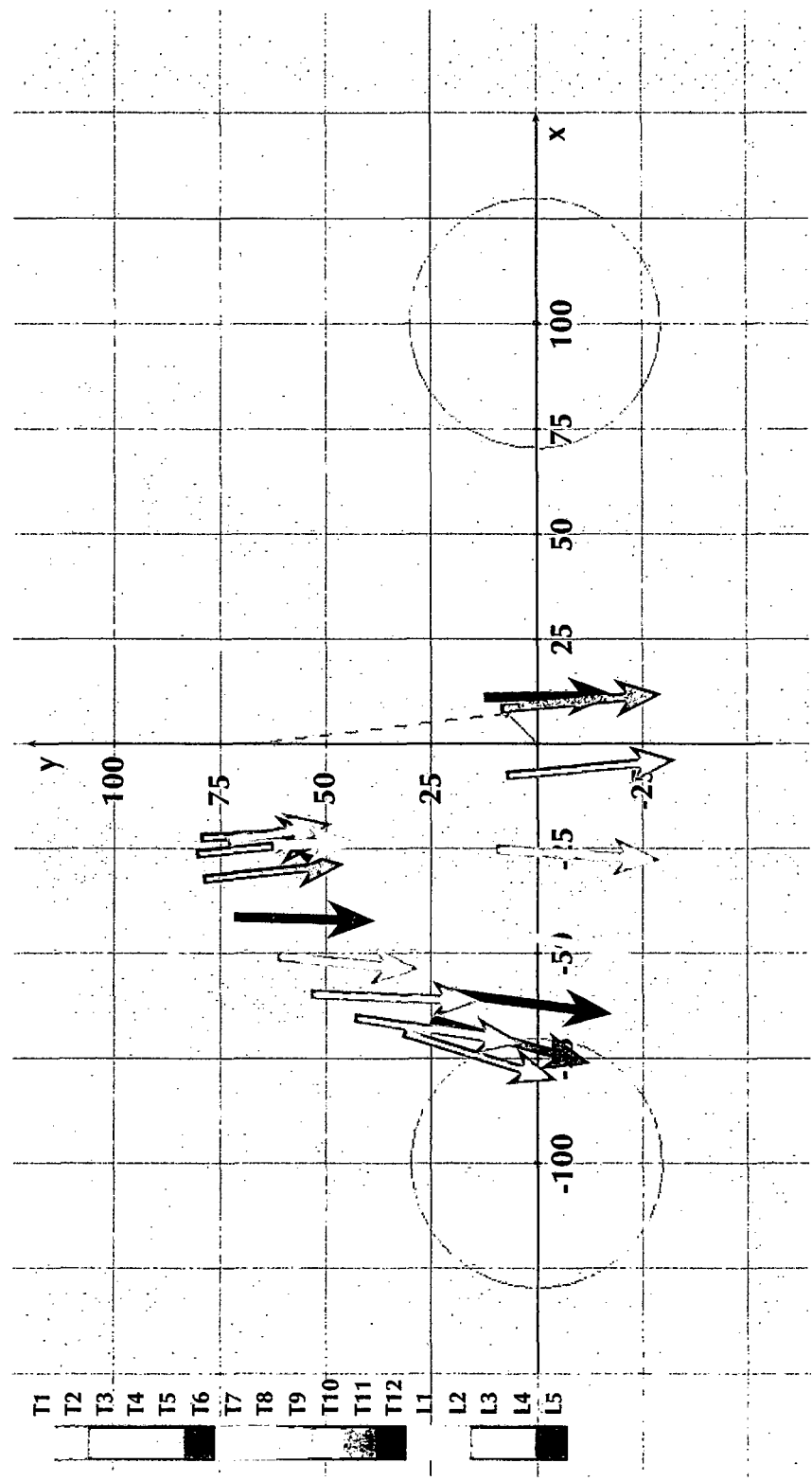
Figure 6A:
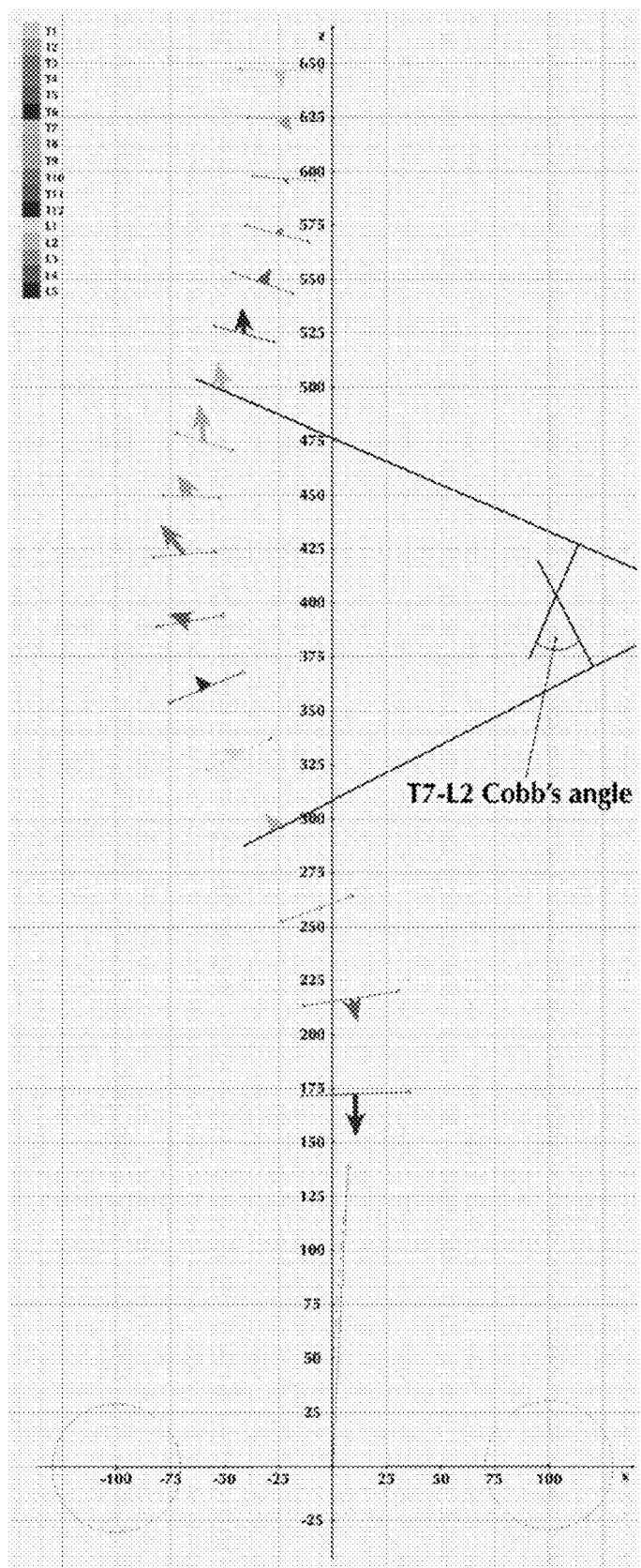
FIGS. 6A-B show visualizations of conventional curve measurements based on vertebra vectors in the frontal and sagittal plane.
Figure 6B:
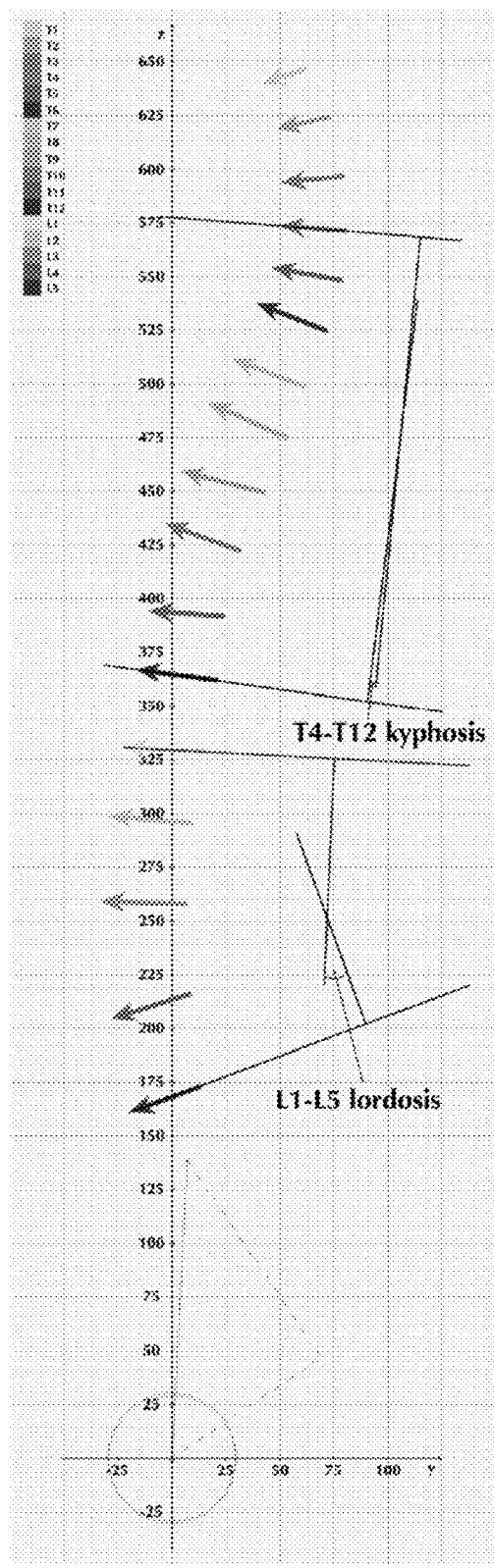

Table 1 shows complete 3D coordinates and calculated parameters of vertebra vectors 1 of the thoracic and lumbar region of a representative scoliotic case presented in FIGS. 5A-5C;

Table 2A shows frontal plane coordinates and calculated parameters of interpedicular and vertebra vectors of the thoracic and lumbar region of a representative scoliotic case presented in FIGS. 5A-5C and illustrated in FIGS. 6A-6B;

Table 2B shows conventional spinal measurement parameter values in the frontal and sagittal plane based on Table 2A.

Figure 7A:
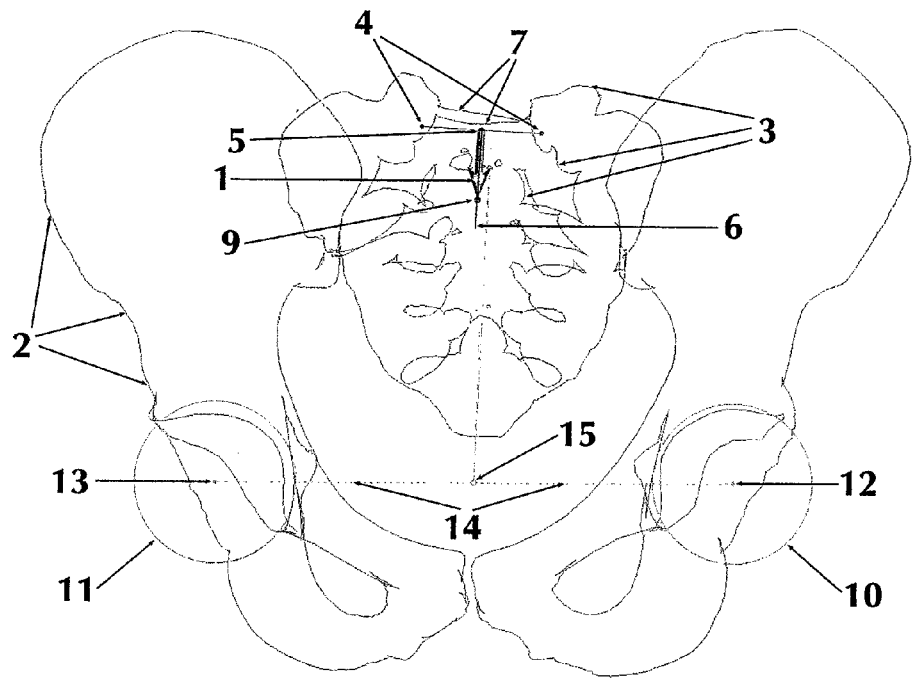
Figure 7B:
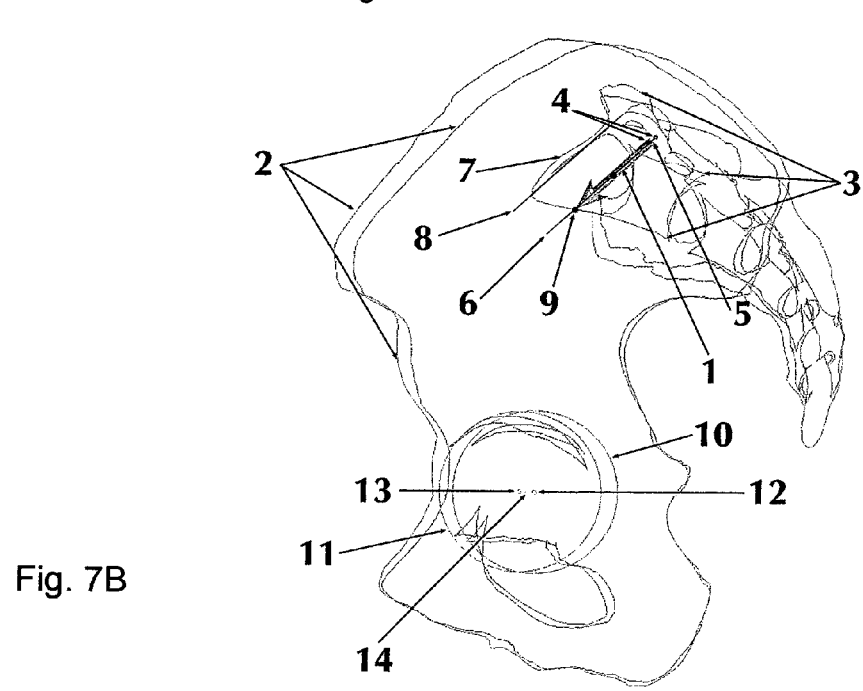
Figure 7C:
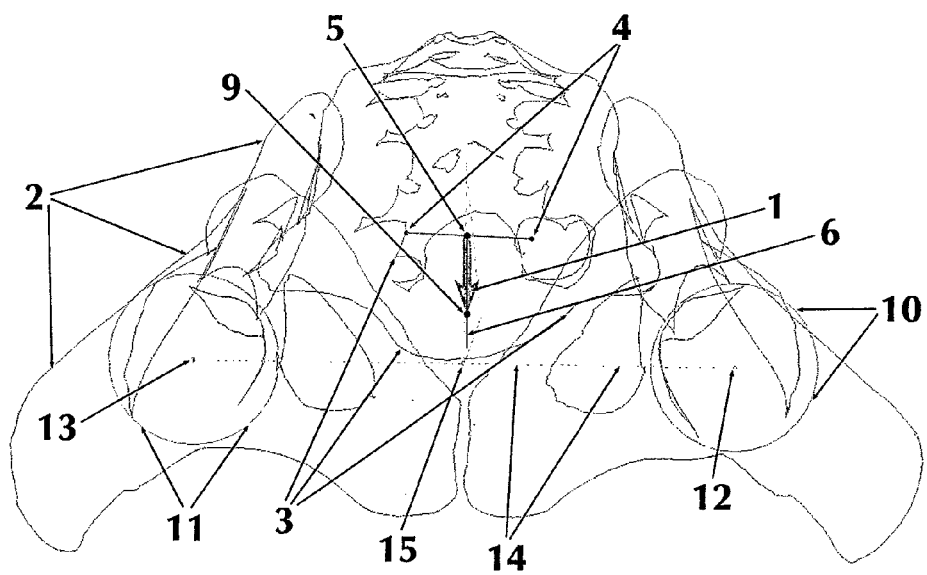
Figure 8A:
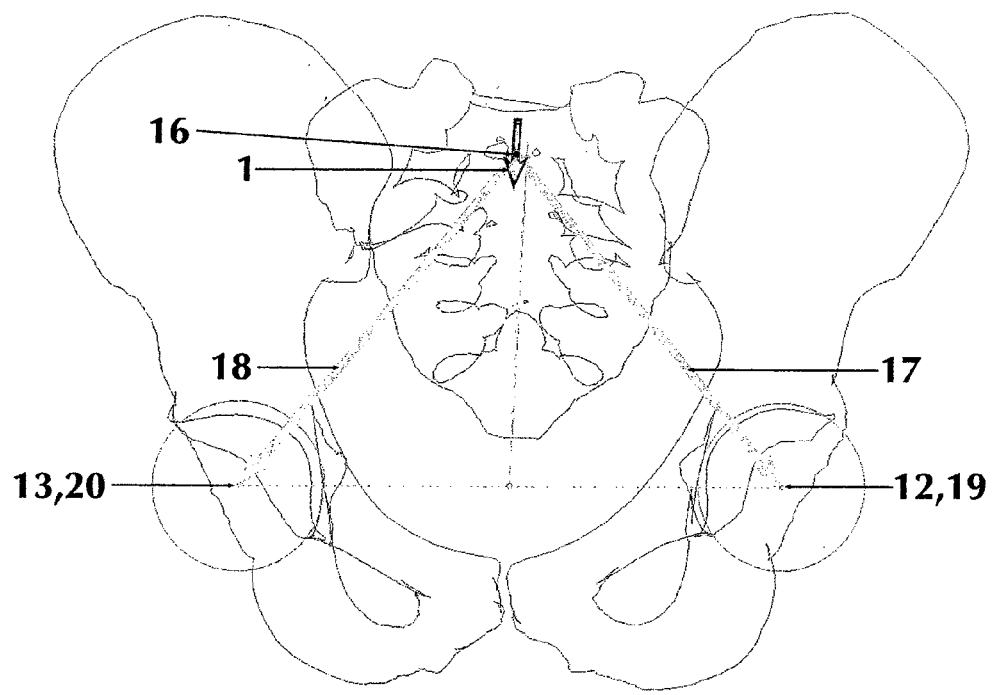
Figure 8B:
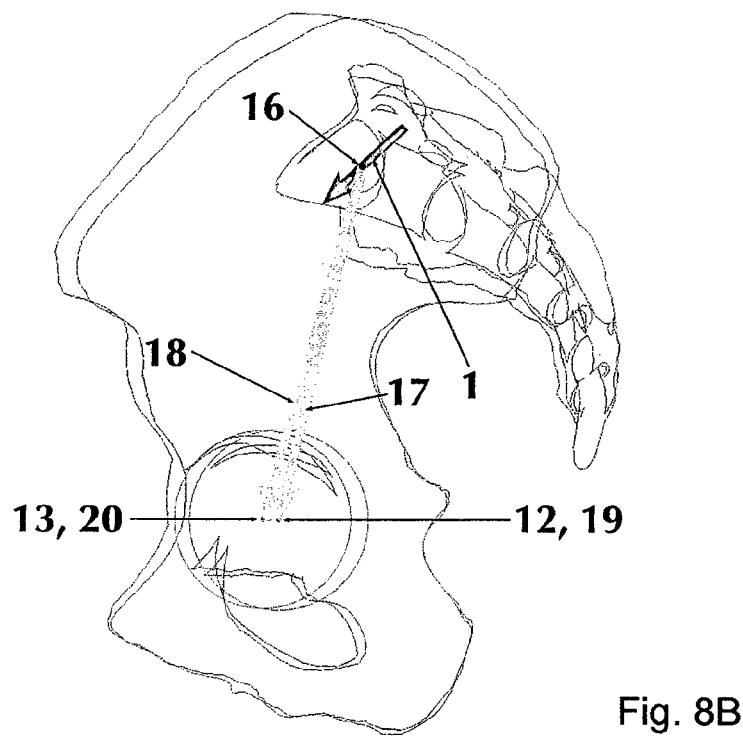
Figure 8C:
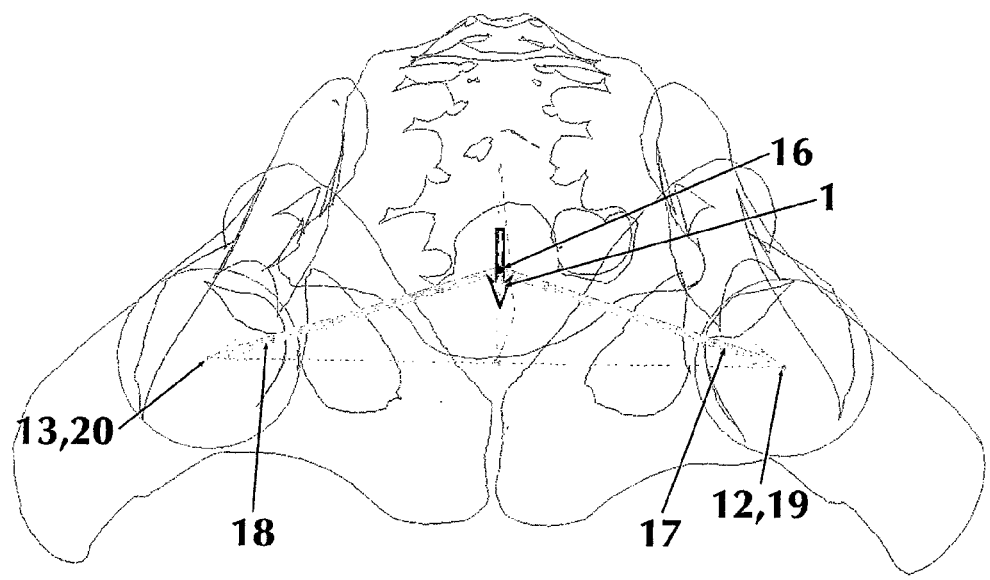
Figure 9A:
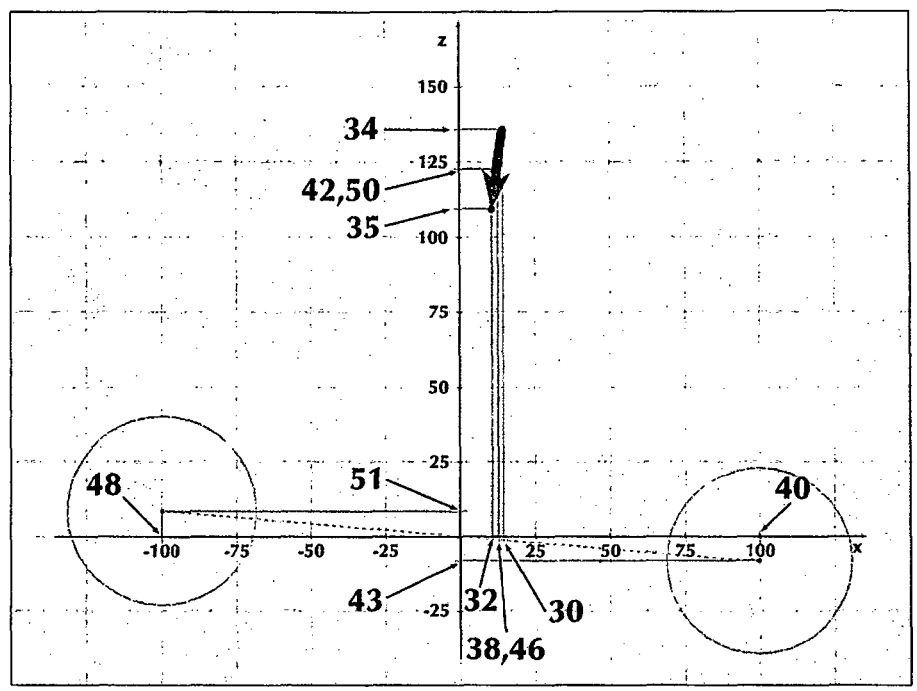
Figure 9B:
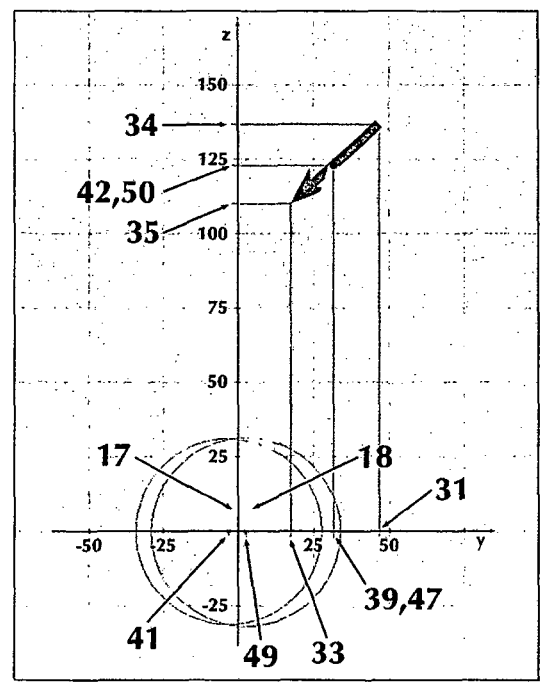
Figure 9C:
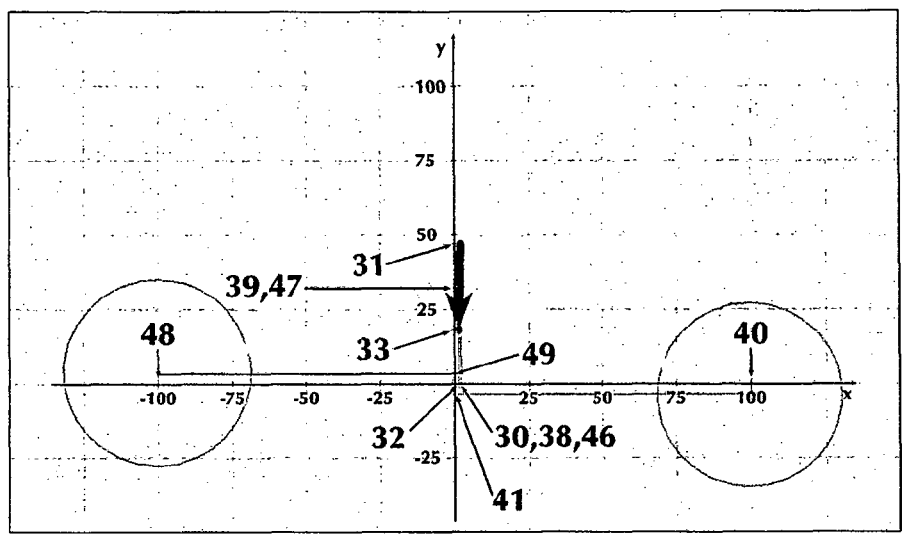
Figure 10A:
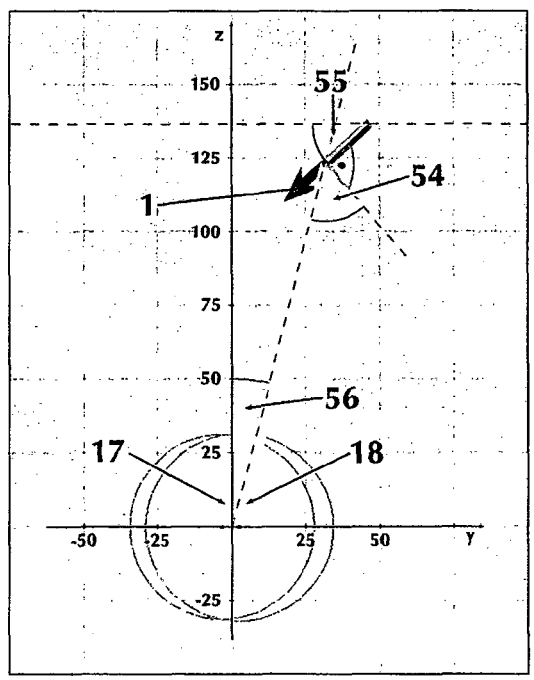
Figure 10B:
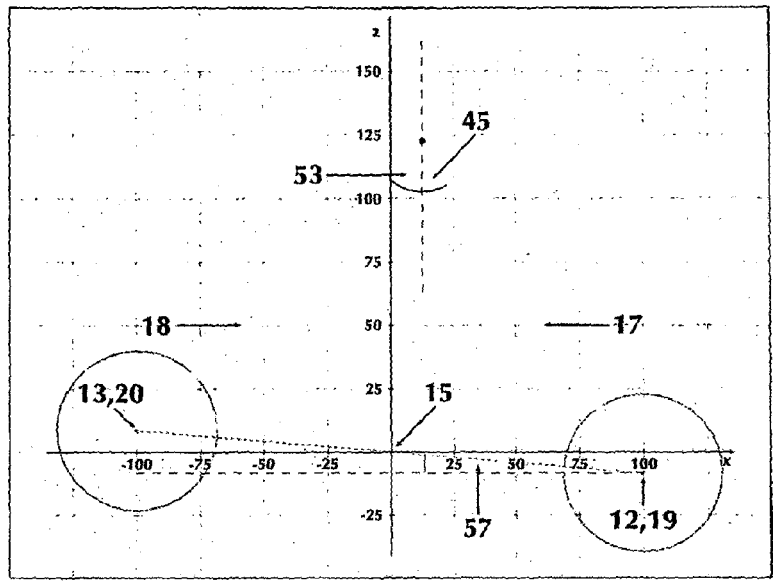
Figure 11A:
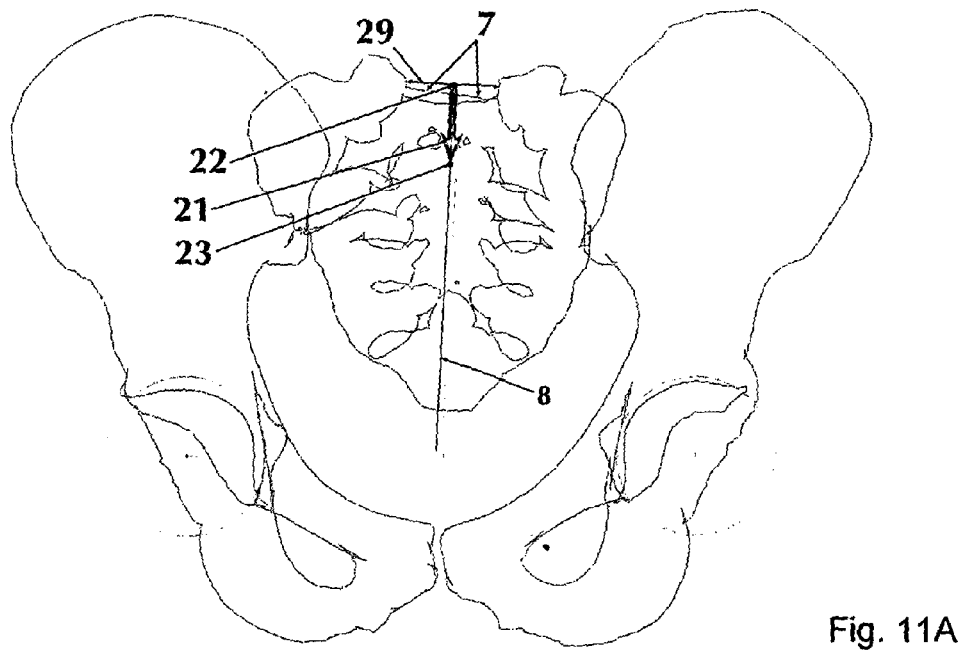
Figure 11B:
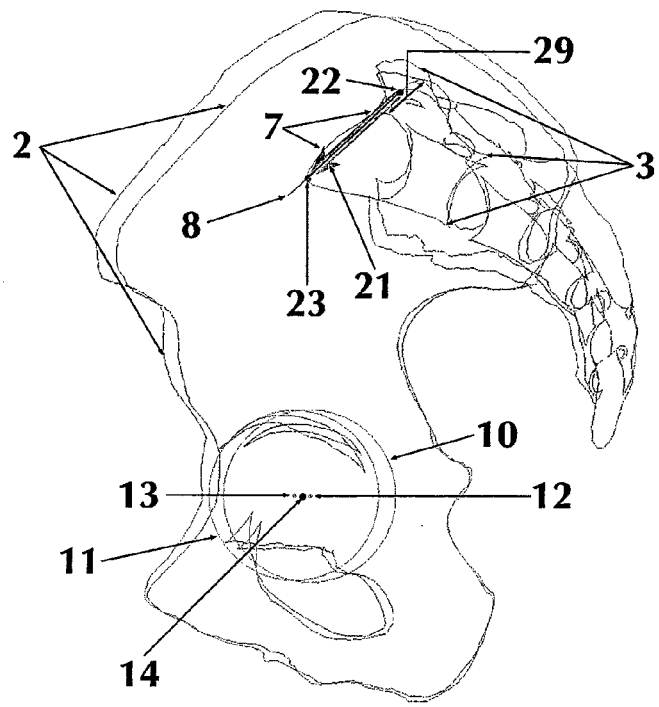
Figure 11C:
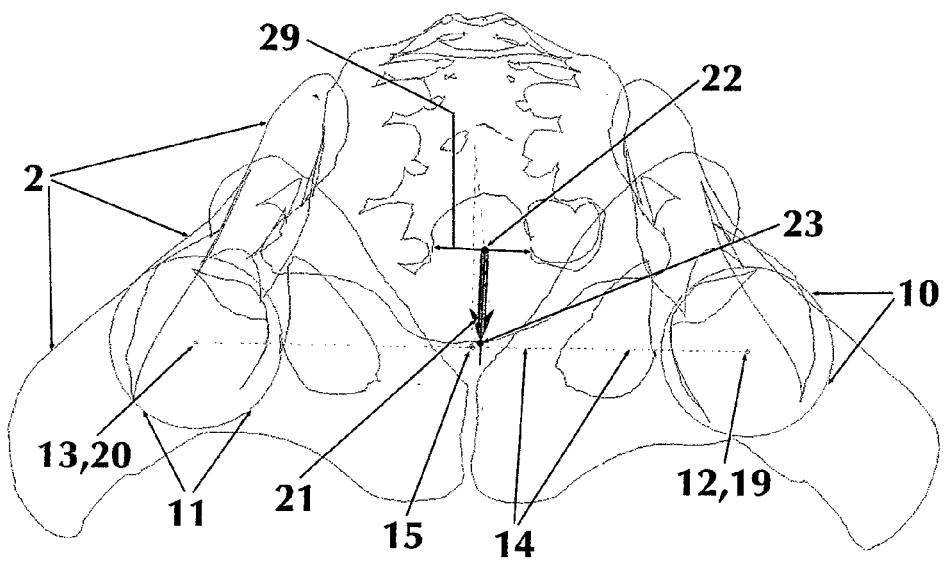
Figure 12A:
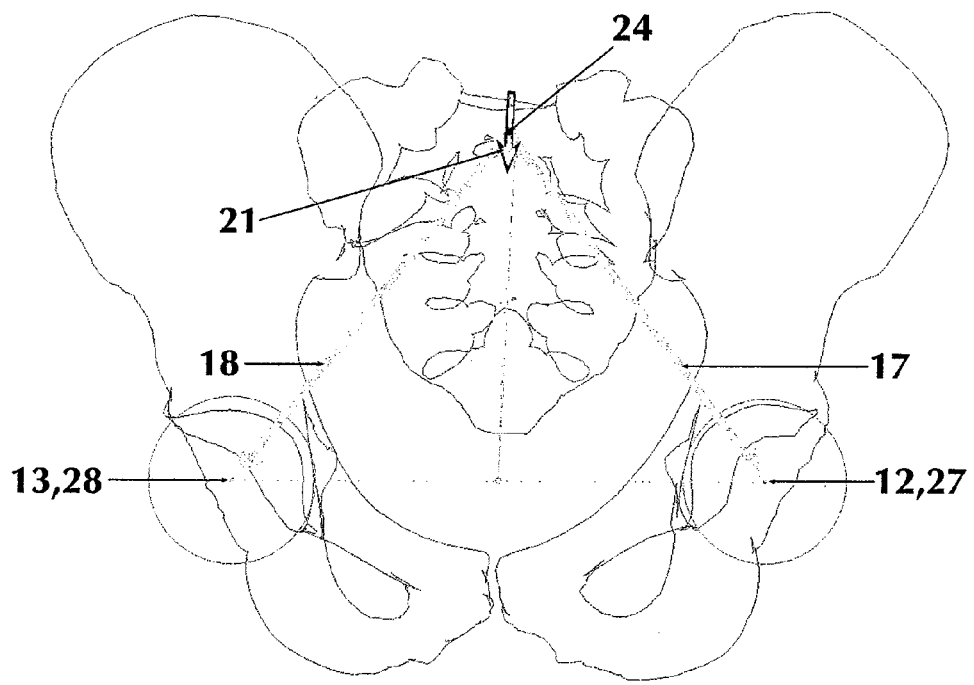
Figure 12B:
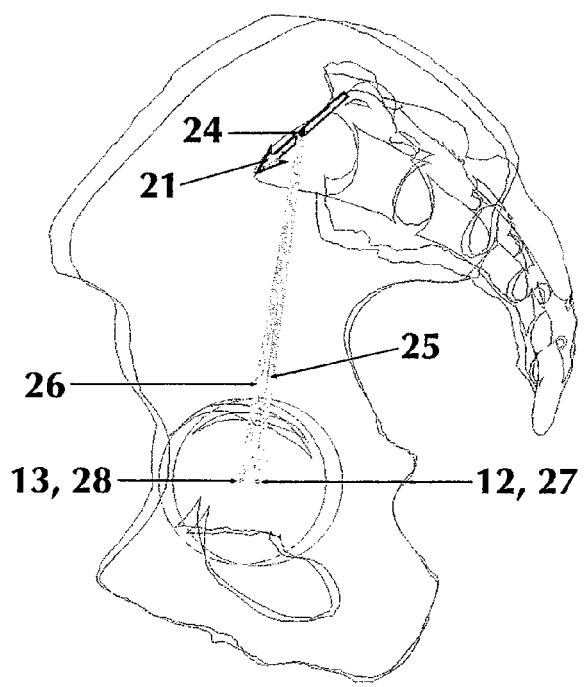
Figure 12C:
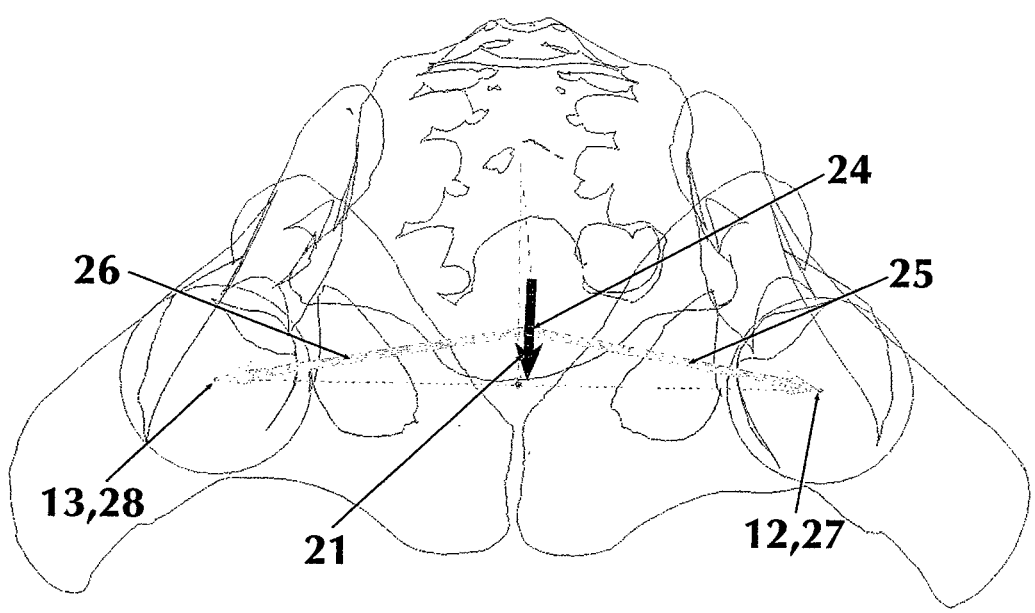
Figure 13A:
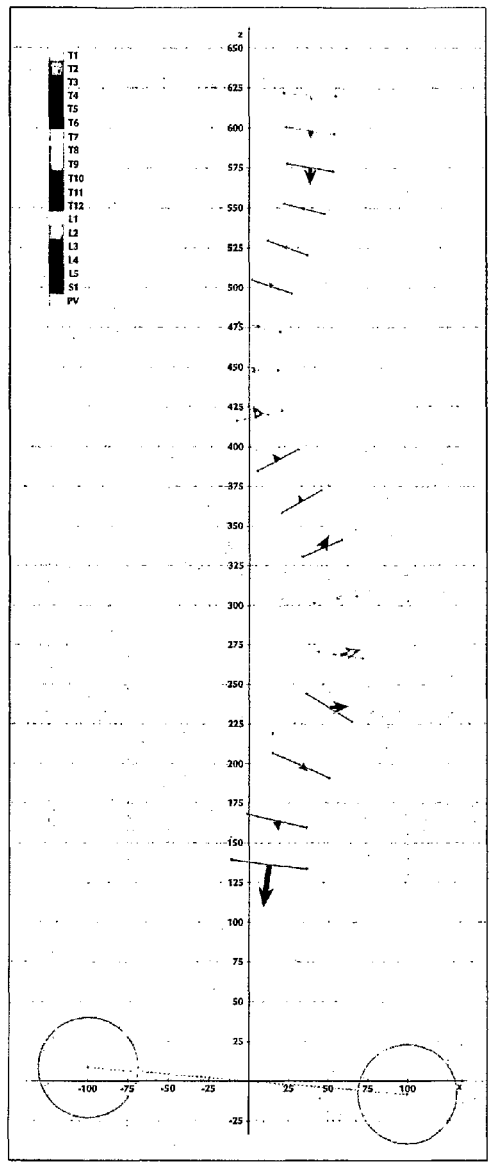
Figure 13B:
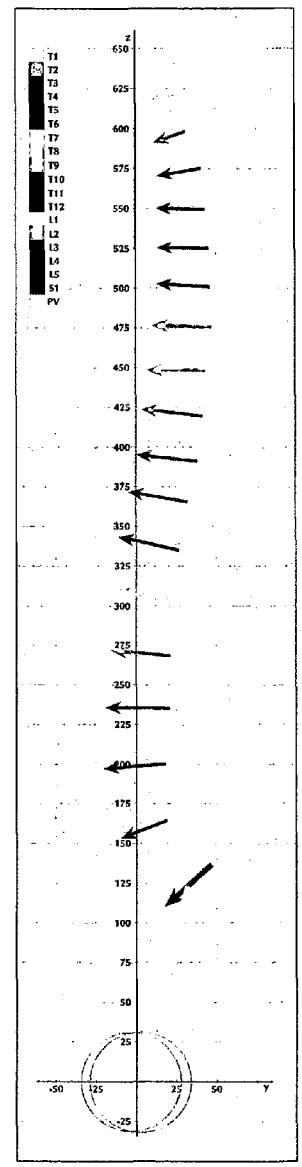
Figure 13C:
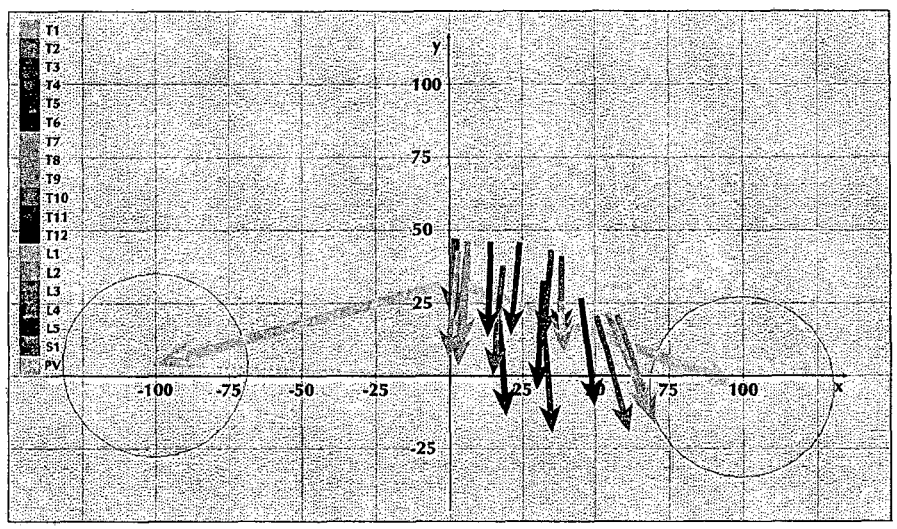

FIGS. 7A-C are illustrations of the sacrum vector and pelvic components for the generation of the sacrum vector in the frontal, sagittal and horizontal plane;

FIGS. 8A-C are illustrations of the pelvis vectors and pelvic components for the generation of the pelvis vectors in the frontal, sagittal and horizontal plane;

FIGS. 9A-C are illustrations for the calculation of sacrum vector and pelvis vector parameters in the frontal, sagittal and horizontal plane;

FIGS. 10A-B are illustrations for the measurement and calculation of conventional pelvic parameters based on the sacrum vector and pelvis vectors in the sagittal and frontal plane;

FIGS. 11A-C are illustrations of the sacrum plateau vector and pelvic components for the generation of the sacrum plateau vector in the frontal, sagittal and horizontal plane;

FIGS. 12A-C are illustrations of the pelvis vectors and pelvic components for the generation of the pelvis vectors based on the sacrum plateau vector in the frontal, sagittal and horizontal plane;

FIGS. 13A-C show visualizations of vertebra vectors of the thoracic and lumbar spinal region with sacrum and pelvis vectors of a patient with a scoliotic spine in the frontal, sagittal and horizontal plane;

FIG. 14 shows a Table A showing indicating complete 3D coordinates and calculated parameters of vertebra vectors 1 of the thoracic and lumbar region of a representative scoliotic case presented in FIGS. 5A-5C;

FIG. 15 shows a Table 2A showing indicating frontal plane coordinates and calculated parameters of interpedicular and vertebra vectors of the thoracic and lumbar region of a representative scoliotic case presented in FIGS. 5A-5C and illustrated in FIGS. 6A-6B; and FIG. 16 shows a Table 2B indicating conventional spinal measurement parameter values in the frontal and sagittal plane based on Table 2A.

DETAILED DESCRIPTION

Vertebra Vector Definition

Figure 1C:
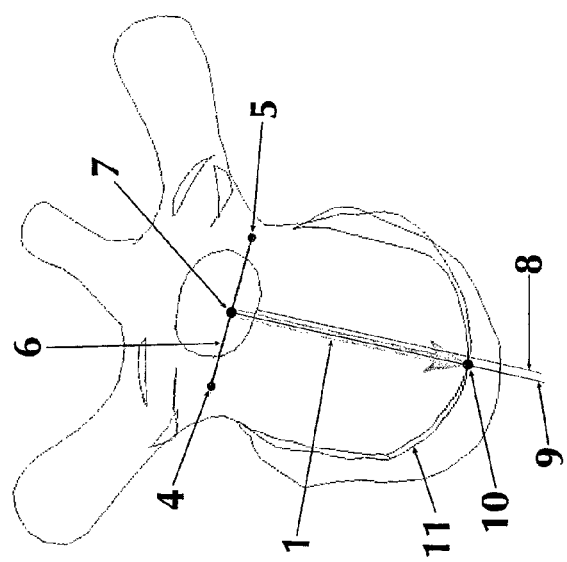
FIGS. 1A-C are illustations of a vertebra vector and vertebral components for the generation of the vertebra vector in the frontal, sagittal and horizontal plane.
Figure 1B:
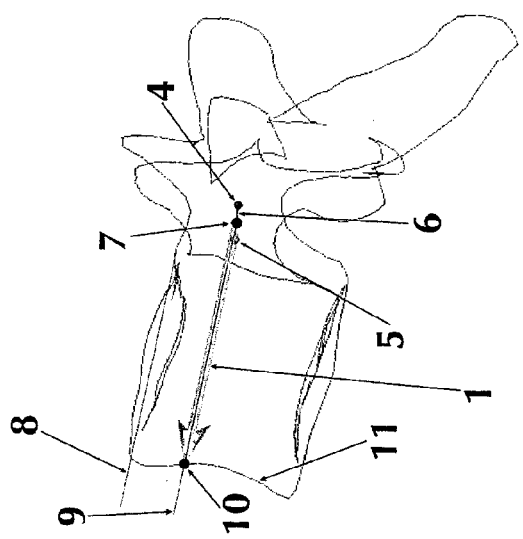
Figure 1A:
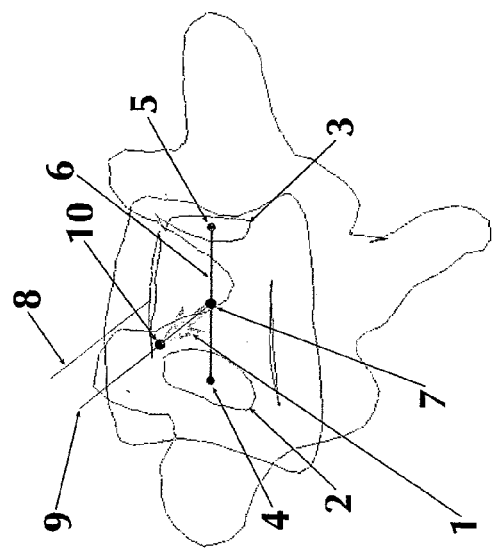

A vertebra vector is a simplified representation of the real vertebra of the spine, based on known vertebral landmarks. A vertebra vector 1 see FIGS. 1A-1C, comprises an initial point 7 "A" and a terminal point 10 "B", with initial point A as the midpoint of a line 6 connecting two pedicular centroids 4 and 5 of a vertebra, and terminal point B as the intersection of the ventral surface contour 11 of a vertebral body and a line 9 originating from point A drawn in the horizontal symmetry axis 8 of the vertebra while contained in a plane parallel to the plane determined by the upper endplate of the vertebral body. Definition of a single vertebra vector 1 is illustrated in the frontal, sagittal and horizontal plane view in FIGS. 1A, 1B and 1C, respectively.

A Calibrated Coordinate System for Determination of Vertebra Vector Coordinates In order to mathematically characterize a vertebra vector 1, determination of coordinate values of the vector 1 is necessary. Therefore, vertebra vectors 1 are placed in a coordinate system that is suitably calibrated as will be disclosed in more detail below. The basic principles and terminology described by Stokes [12] are utilized to create this coordinate system. An axis x of the coordinate system is the interacetabular line connecting the two acetabular centers 12 and 13 of the pelvis in horizontal plane, see FIGS. 2A-2C. An axis y is the line perpendicular to the frontal plane and the interacetabular line, with an origin 14 at its midpoint. An axis z is perpendicular to the horizontal plane and the axis x at the origin 14.

Figure 2A:
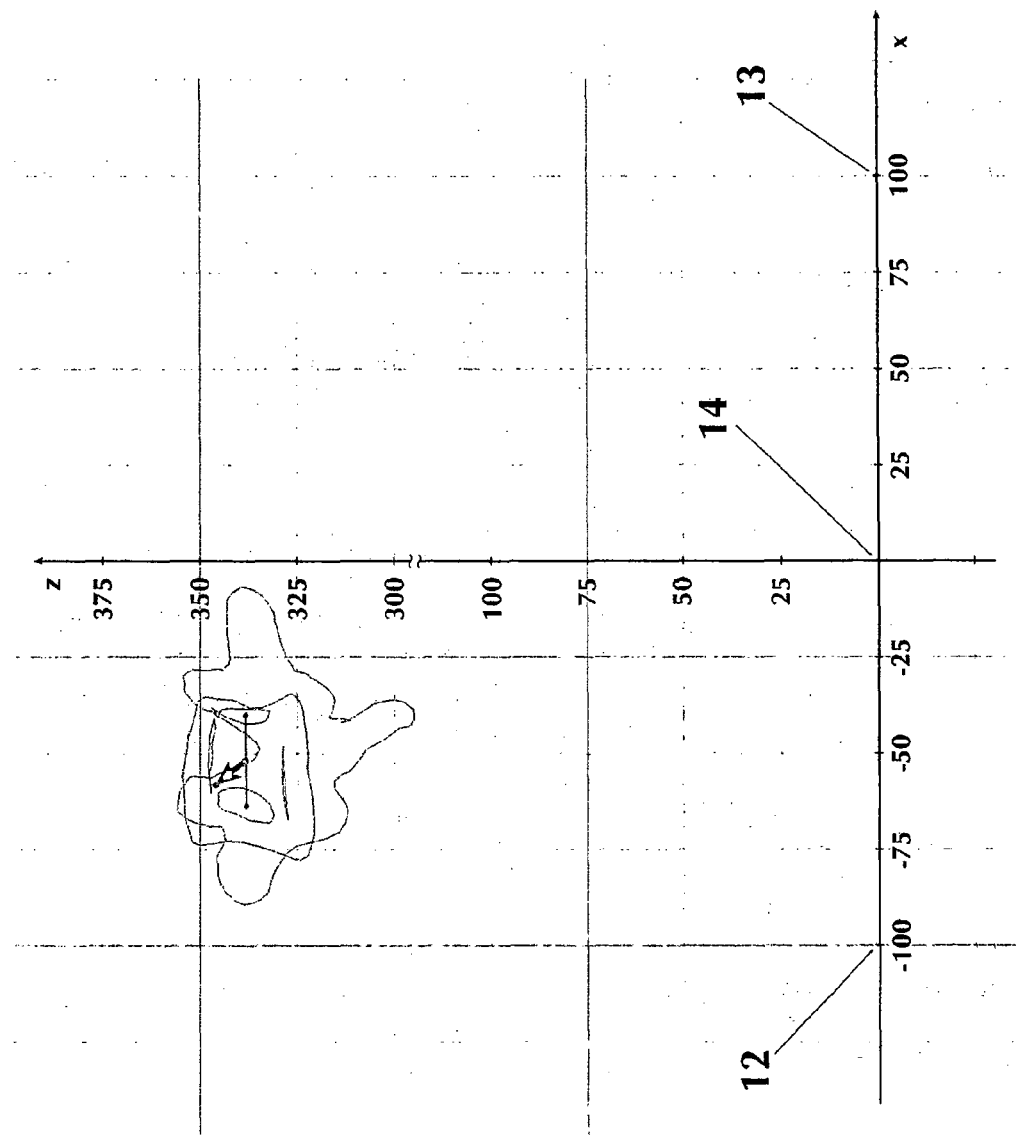
FIGS. 2A-C are illustrations for the creation of the calibrated coordinate system in the frontal, sagittal and horizontal plane.
Figure 2B:
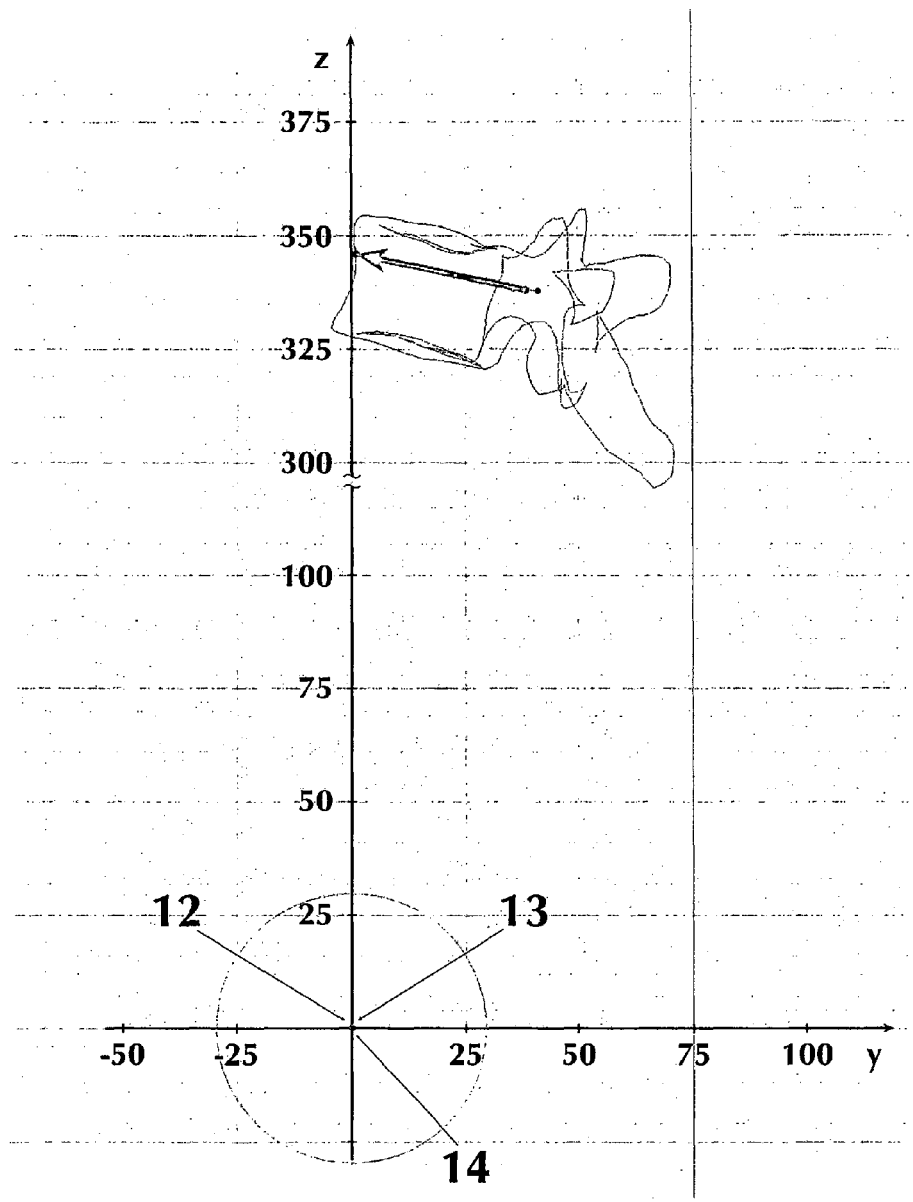
Figure 2C:
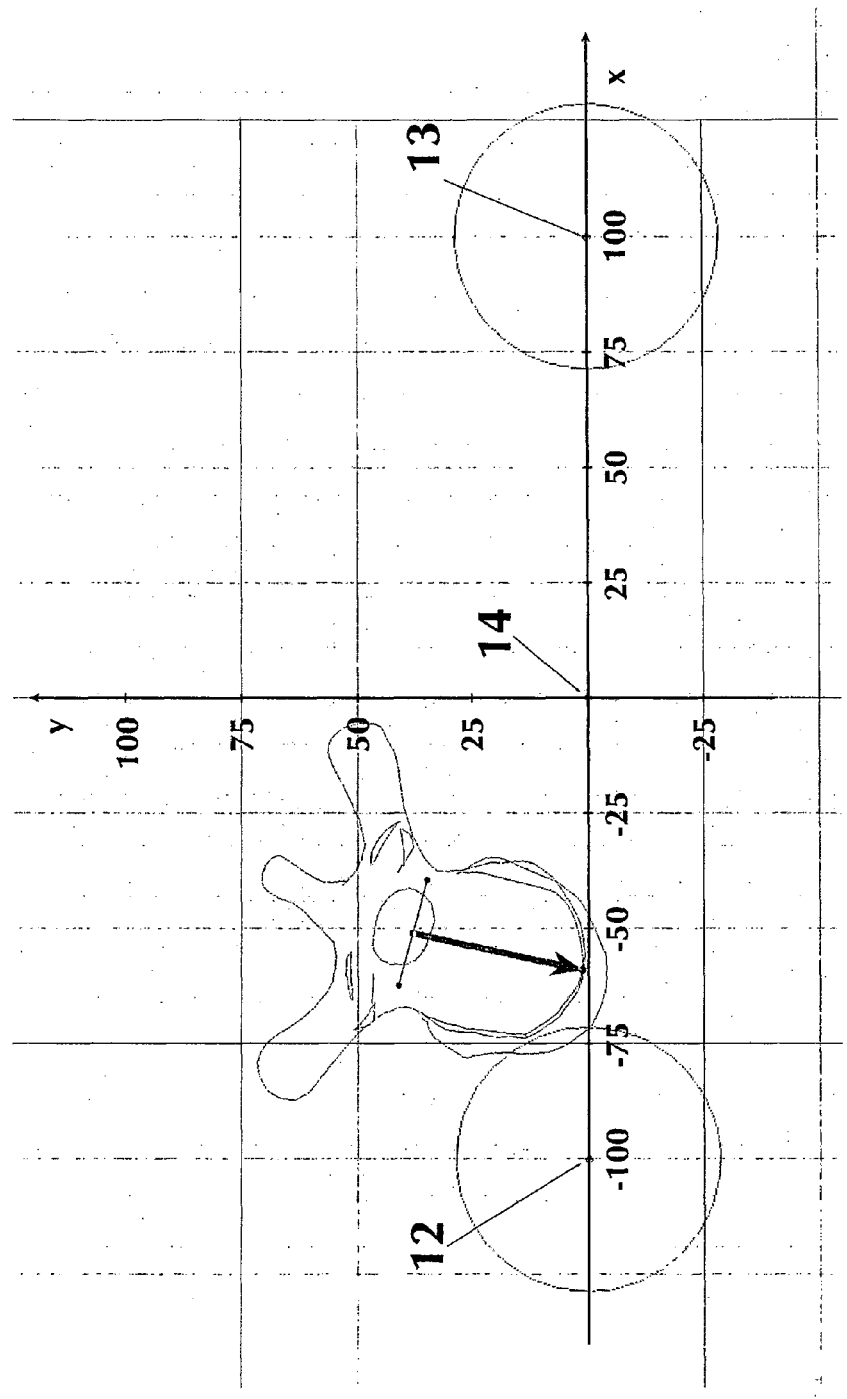

Calibration of the coordinate system is based on the length of the interacetabular line in the horizontal plane view. The calibration scale is identical for the axes x, y and z. To create a suitable scale, a value of 100 is assigned to the distance between the origin 14 and either of the acetabular centers 12 and 13; thus, the total interacetabular distance is dividen in 200 units. The calibrated coordinate system in the frontal, sagittal and horizontal plane is illustrated in FIGS. 2A, 2B and 2C, respectively.

Calculation of Vertebra Vector Parameters

Figure 3A:
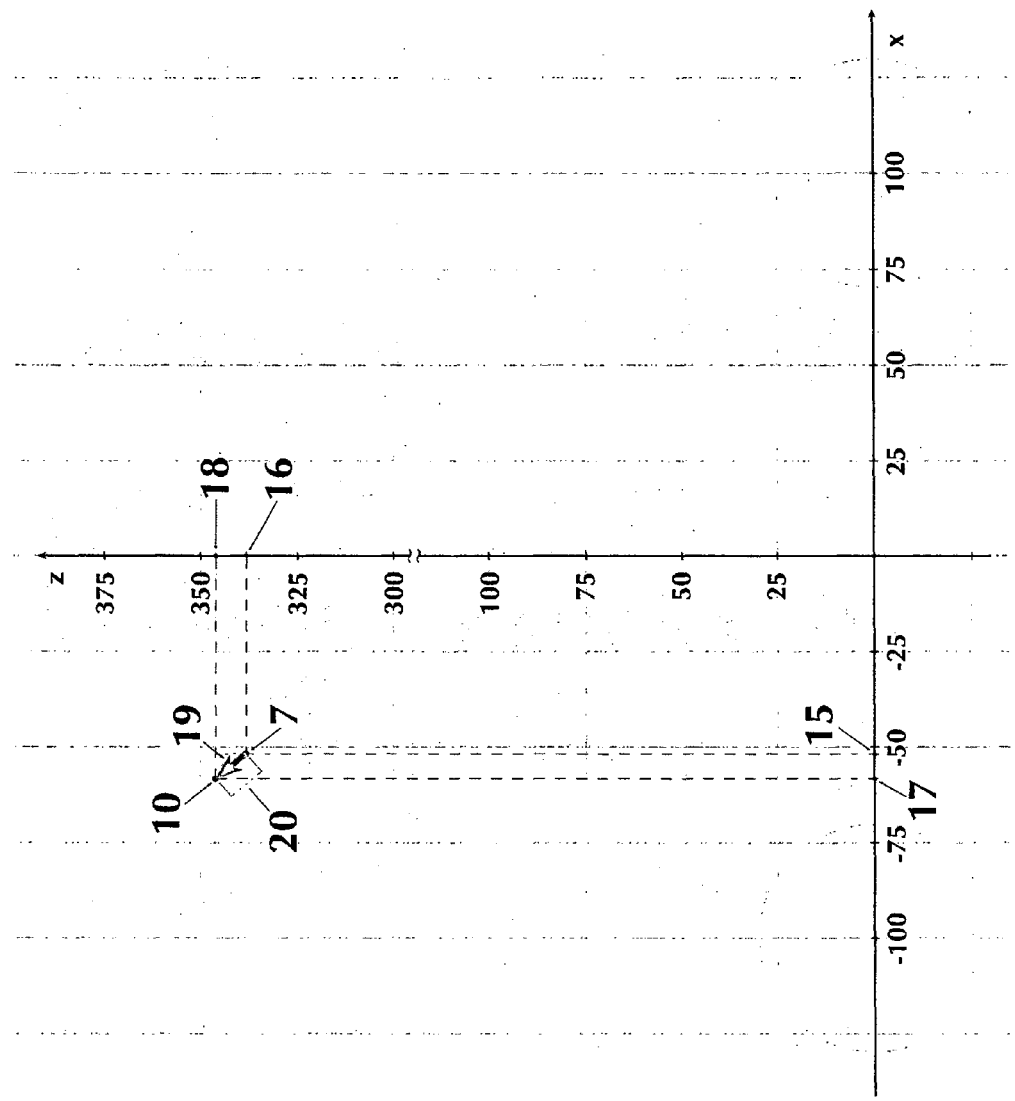
FIGS. 3A-C are illustrations for the calculation of vertebra vector parameters in the frontal, sagittal and horizontal plane.
Figure 3B:
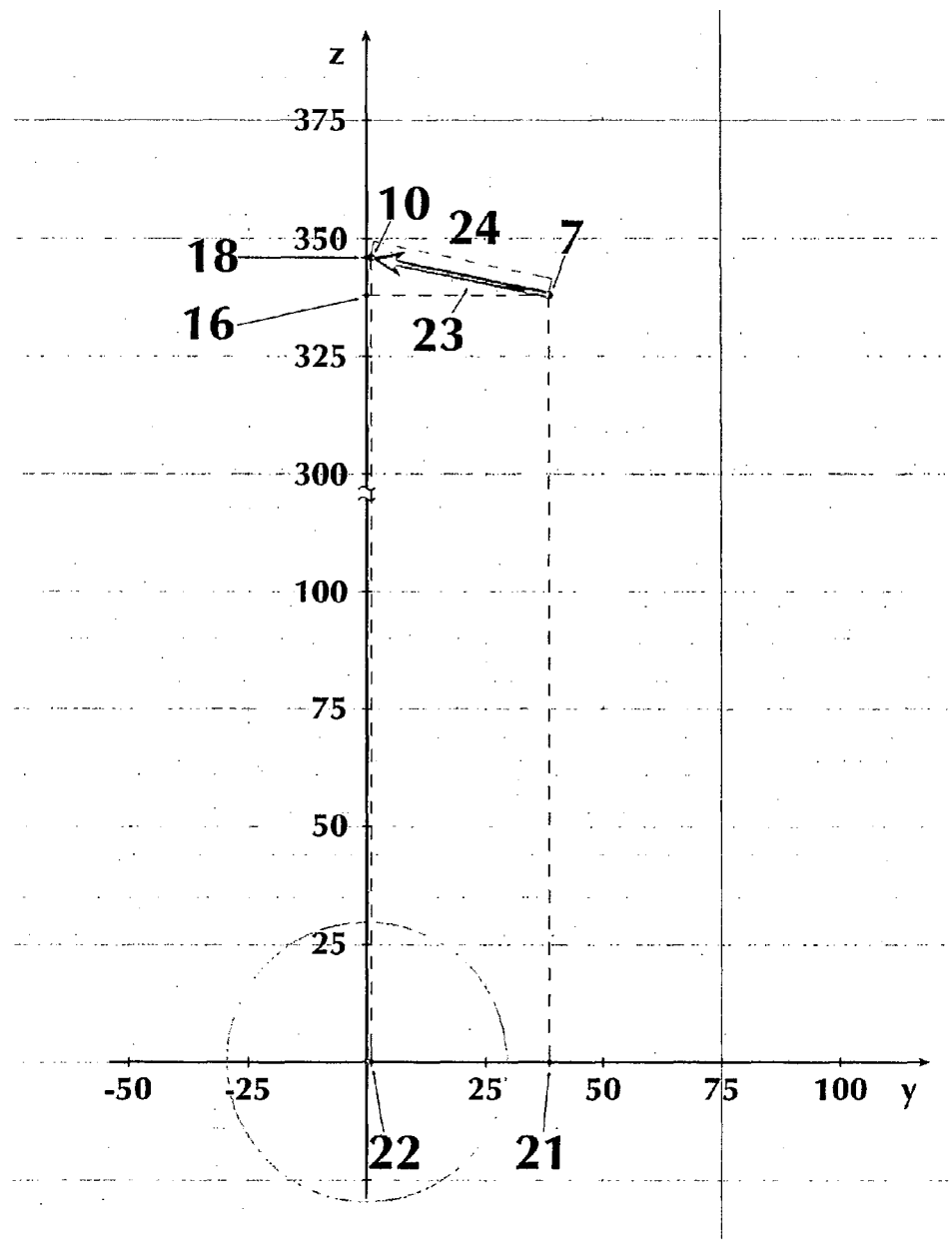
Figure 3C:
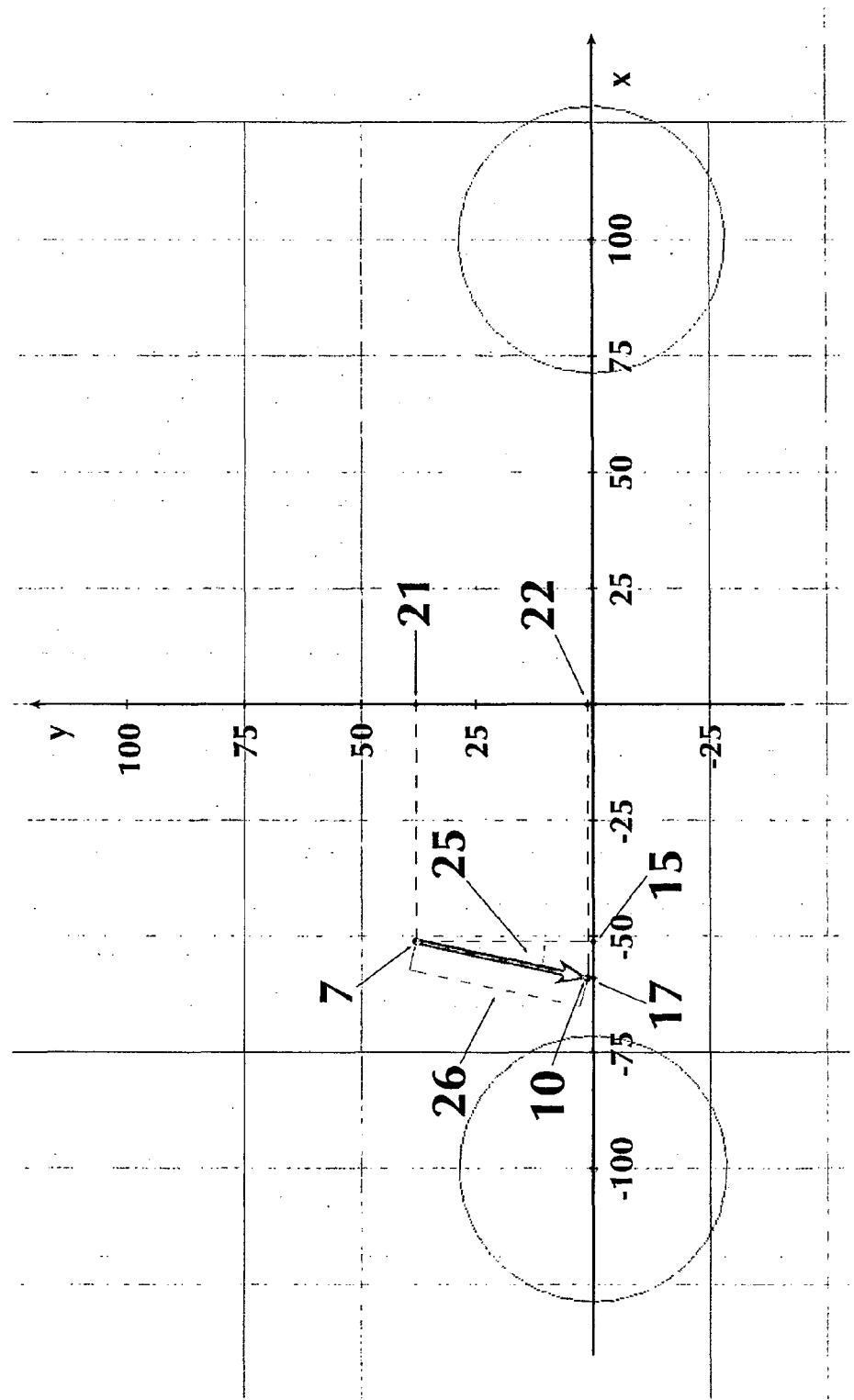

Following the creation of the coordinate system and placement of vertebra vector 1 inside, coordinates of each vector point are determined in all three planes by using basic geometric and vector algebraic methods, as illustrated in FIGS. 3A-3C.

Coordinates 15, 16 of initial point A and coordinates 17, 18 of terminal point B of vector 1 in the frontal plane are $A(A_x; A_z)$ and $B(B_x; B_z)$. Coordinates 15, 16, 17, 18 of vector AB are therefore $AB(B_x-A_x; B_z-A_z)$. The lateral translation (also called lateral ejection [23,24]) of the vertebra vector 1 from the axis z is determined by the direct value of coordinate 17 $B_x$, while the projected length 20 of vector 1 in the frontal plane is calculated as $$d_{ABF} = \sqrt{(A_z-B_z)^2 + (A_x-B_x)^2}$$

and vector angle 19 $\alpha_F$ relative to the axis z is calculated by using the function $$\tan\alpha_F = AB_z/AB_x.$$

Coordinates 21, 16 of initial point A and coordinates 22, 18 of terminal point B of vector 1 in the sagittal plane are $A(A_y; A_z)$ and $B(B_y; B_z)$. Coordinates 21, 16, 22, 18 of vector 1 are therefore $AB(B_y-A_y; B_z-A_z)$. The projected length 24 of vector 1 in the sagittal plane is calculated as $$d_{ABS} = \sqrt{(A_z-B_z)^2 + (A_y-B_y)^2}$$

and vector angle 23 $\alpha_S$ relative to the axis y is calculated by using the function $$\tan\alpha_S = \frac{AB_z}{AB_y}.$$

Coordinates 15, 21 of initial point A and coordinates 17, 22 of terminal point B of vector 1 in the horizontal plane are $A(A_x; A_y)$ and $B(B_x; B_y)$. Coordinates of vector 1 are therefore $AB(B_x-A_x; B_y-A_y)$. The lateral translation (also called lateral ejection [23,24]) from the axis y is again equal to the value of coordinate 17 $B_x$ while the projected length 26 of vector 1 in the horizontal plane is calculated as $$d_{ABH} = \sqrt{(A_y-B_y)^2 + (A_x-B_x)^2}$$

and vector angle 25 $\alpha_H$ relative to the axis y is calculated by using the function $$\tan\alpha_H = \frac{AB_x}{AB_y}.$$

Thus, combined values for each vertebra vector 1 containing its 3D parameters in the frontal, sagittal and horizontal plane are to be presented as vector point coordinates $A(A_x; A_y; A_z)$ and $B(B_x; B_y; B_z)$, 3D vector coordinates $AB(X;Y;Z)$ and vector angles $\alpha_F$, $\alpha_S$, and $\alpha_H$, respectively, see Table 1 as shown in FIG. 14 for vertebra vector 3D parameters of vertebrae $T_1$-$L_V$).

Calculation of Interpedicular Line Coordinates and its Angle Relative to the Axis x Coordinates 28, 29 of the left pedicular centroid 4 and coordinates 30, 31 of the right pedicular centroid 5 of each vertebra in the frontal plane are determined as $PCL(PCL_x; PCL_z)$ and $PCR(PCR_x; PCR_z)$, see FIGS. 4A and 4B. The line 6 connecting PCL and PCR is interpedicular line $IP_{PC}$. In a scoliotic spine segment, most vertebrae of the frontal curves are tilted or rotated in the frontal plane, therefore the interpedicular line $IP_{PC}$ is not perpendicular to the axis z. Based on direction of the tilting, one of the pedicular centroids 4 and 5, i.e., PCR or PCL, is always found more distant from the axis x than the other. In order to calculate the angle of $IP_{PC}$ relative to the axis x, interpedicular line $IP_{PC}$ is taken as a vector, called interpedicular vector IPR, and the initial point determining the direction of the vector is chosen as the pedicular centroid more distant from the axis x.

As a consequence, when PCR is more distant from the axis x than PCL, interpedicular line $IP_{PC}$ is assigned to a direction right-to-left and is called interpedicular vector IPR. Likewise, when PCL is more distant from the axis x than PCR, interpedicular line $IP_{PC}$ is assigned to a direction left-to-right and is called interpedicular vector IPL.

Coordinates of interpedicular vector IPR are $IPR(PCR_x-PCL_x; PCR_z-PCL_z)$ and angle 32 $\alpha_{IPR}$ relative to the axis x is calculated by using the function $$\tan\alpha_{IPR} = \frac{IPR_z}{IPR_x}.$$

Coordinates of interpedicular vector IPL are $IPL(PCR_x-PCL_x; PCR_z-PCL_z)$, and angle 34 $\alpha_{IPL}$ relative to the axis x is calculated by using the function $$\tan\alpha_{IPL} = \frac{IPL_z}{IPL_x}.$$

Figure 4A:
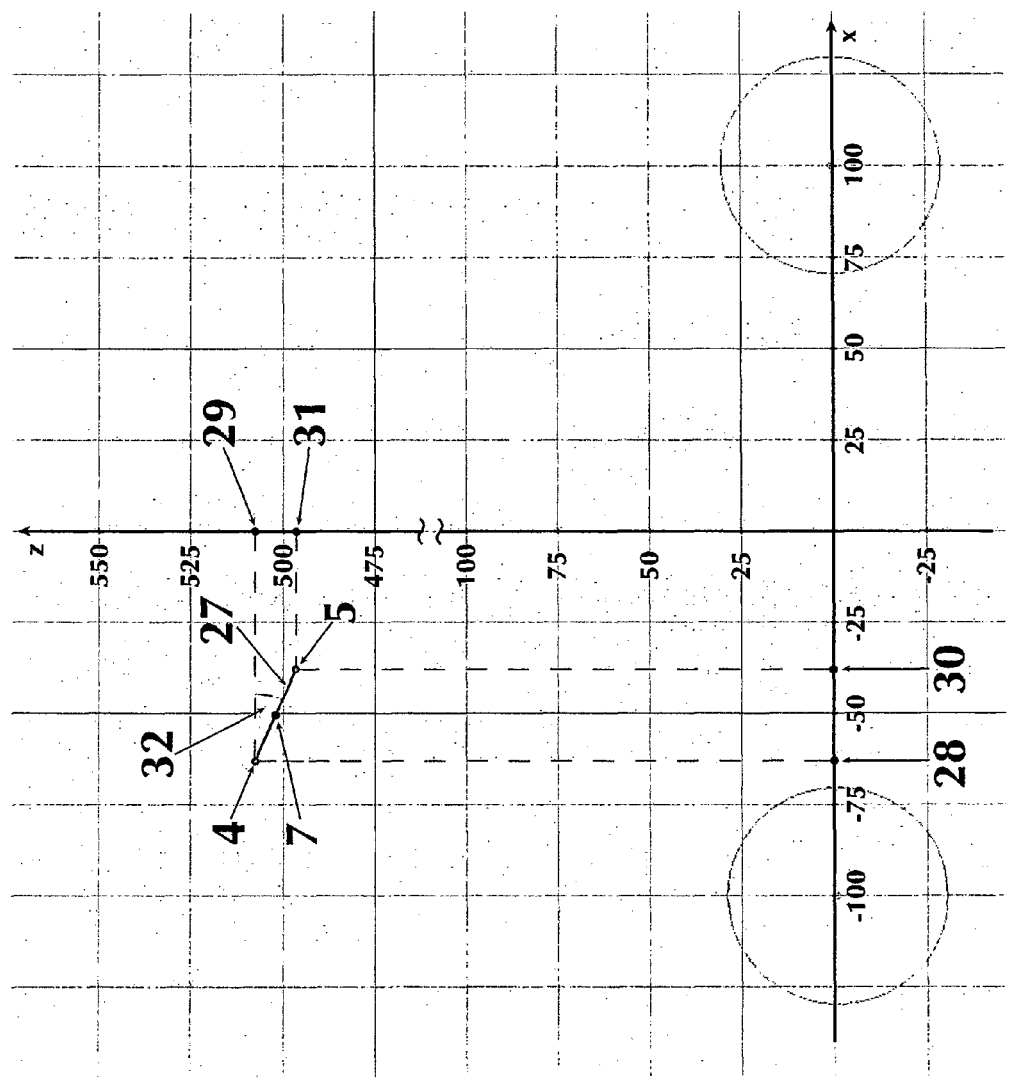
FIGS. 4A-B are illustrations for the calculation of interpedicular vector parameters in the frontal plane, for a right convex and a left convex spinal curve.
Figure 4B:
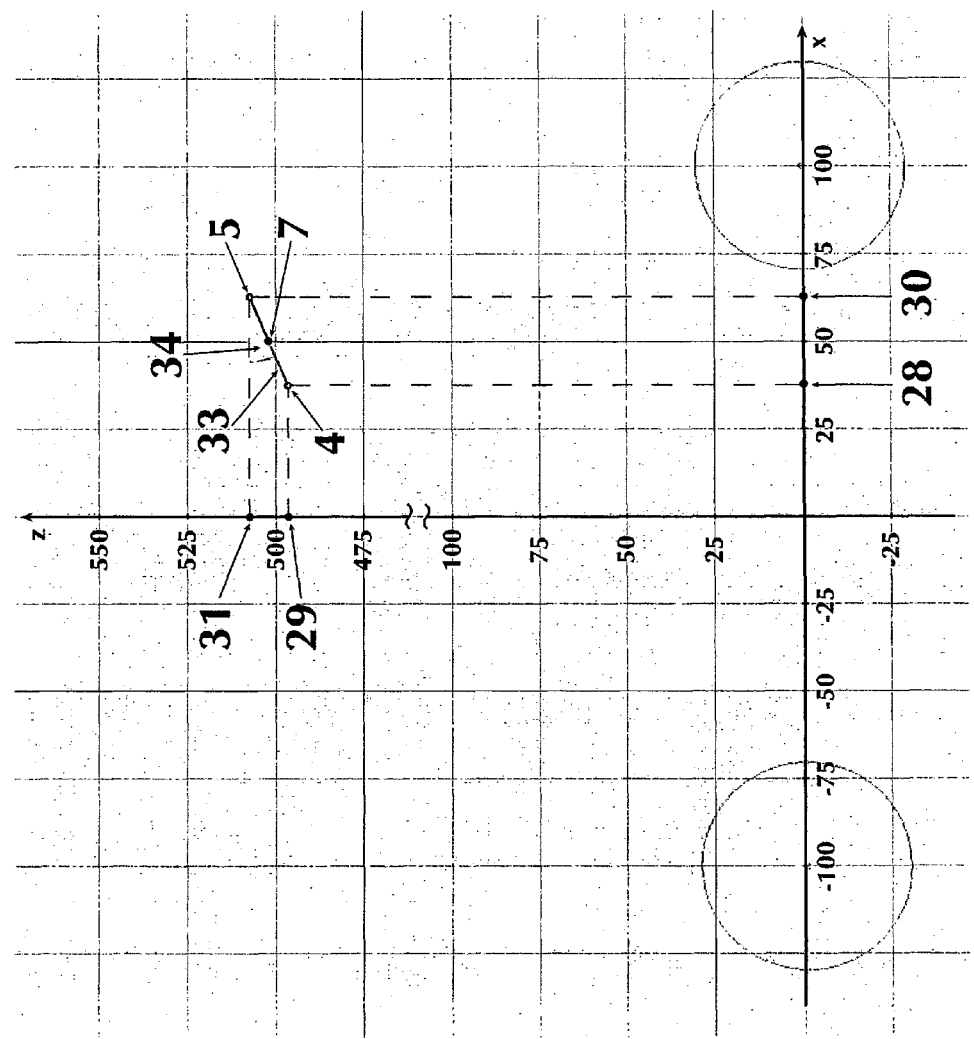

Calculation of angles 32, 34 $\alpha_{IPR}$ and $\alpha_{IPL}$ is illustrated in FIGS. 4A and 4B, respectively.

Three-Dimensional Visualization of the Scoliotic Spine in the Thoracic and Lumbar Region with Vertebra Vectors Visualization of the scoliotic spine showing a major right convex thoracolumbar curve (Lenke type IA [1]) is illustrated in FIGS. 5A-5C. Vertebra vectors $T_1$-$L_V$ of the thoracic and lumbar region are shown in FIG. 5A in the frontal plane, in FIG. 5B in the sagittal plane, and FIG. 5C in the horizontal plane. For easier differentiation of vertebrae from one another, especially in the horizontal plane, a color-coded key shown in Legend of FIG. 5A-B-C is used.

Measurement of Spinal Curve Angles According to the Conventional Cobb's Method in the Frontal and Sagittal Plane The use of vertebra vectors allows for conventional spinal curve measurements in the frontal and sagittal plane as described by Cobb [25].

Frontal plane Cobb's angle values are determined according to the conventional method. The only difference compared to the original method is that instead of measurement of angulation between lines determined by the upper endplate of the upper end-vertebra and the lower endplate of the lower end-vertebra of the curve, angulation between the interpedicular line of the same two vertebrae is calculated, by a summation of values for the interpedicular vector angle ($\alpha_{IPR}$ or $\alpha_{IPL}$) of the same two vertebrae of the curve is made.

Sagittal plane curvature angle values are also determined almost identical to the conventional method. The only difference compared to the original method is that instead of angulation measurement between lines determined by the upper and lower endplate of the vertebral body of $Th_4$ and $Th_{12}$ for kyphosis and of $L_1$ and $L_F$ for lordosis, a summation of vector angle $\alpha_S$ of the same two pairs of vertebrae is carried out.

Complete Three-Dimensional Characterization of the Spine in the Thoracic and Lumbar Region with Parameters Based on Vertebra Vectors Demonstration of 3D parametric values of vertebra vectors of the thoracic and lumbar region of the scoliotic spine illustrated in FIGS. 5A-5C are shown in Table 1. Parametric values of $A(A_x;A_y;A_z)$, $B(B_x;B_y;B_z)$, AB(X;Y;Z), and vector angles $\alpha_H$, $\alpha_F$, and $\alpha_S$ are shown for each vertebra as determined and calculated according to the methods described above.

Conventional spinal parameteric values in the frontal plane as the Cobb's angle of the right convex thoracolumbar curve, and in the sagittal plane as thoracic kyphosis and lumbar lordosis, could be also measured based on parameters of vertebra vectors and the corresponding interpedicular lines, as detailed above and shown in Tables 2A and 2B as found in FIGS. 15-16.

Sacrum Vector Definition

The coordinate system used for positioning the vertebra vectors is determined by the position of the two acetabular centers of the pelvis. The x axis of the coordinate system is the axis defined by the acetabular centers. The midpoint of the distance between the two acetabular centers is the origo of the coordinate system, from which point axes y and z are originated. In normal case the origo falls exactly to the mediolateral axis of the body, serving as a truly symmetrical, central starting point for the coordinate system. But this is not always true, especially not if the pelvis is deformed or there is a length-discrepancy between the two lower limbs. To determine a possible pelvic deformation and to further enhance the coordinate system outlined above for vertebra vectors, we introduce the terms of sacrum vector and pelvis vectors according to the following.

The sacrum vector 1' is determined by exactly the same principles as vertebra vectors for the thoracic and lumbar spine, as described above in FIG. 7A-C. For the sacrum vector 1' only the first sacral vertebra 3' (vertebra S1) of the pelvis 2' is used, therefore sacrum vector is identical to the vertebra vector S1. Initial point $A_{S1}$ (5') is the midpoint of the interpedicular line formed between the pedicular centroids 4' of vertebra S1. Sacrum vector line 6' is drawn in the horizontal symmetry axis of the vertebra S1 while contained in a plane parallel to the plane determined by the sacrum plateau 7' of the pelvis. Terminal point $B_{S1}$ (9') of sacrum vector is the intersection of the sacrum vector line 6' and the ventral surface of the sacrum.

Calculation of Sacrum Vector Parameters

For defining the coordinates of the sacrum vector, it is placed inside the same 3D coordinate system that is used for the vertebra vectors. Principles for making this coordinate system are exactly identical to the vertebra vectors.

Coordinates of each vector point are determined in all three planes by using basic geometric and vector algebraic methods, as illustrated in FIGS. 9A-C.

Coordinates 30', 34' of initial point $S1_A$ and coordinates 32', 35' of terminal point $S1_B$ of vector 1' in the frontal plane are $A_{S1}(A_x;A_z)$ and $B_{S1}(B_x;B_z)$. Coordinates 30',34',32',35' of vector $AB_{S1}$ are therefore $AB_{S1}$ $(B_x-A_x;B_z-A_z)$. The lateral translation (also called lateral ejection [23,24]) of the vertebra vector 1' from the axis z is determined by the direct value of coordinate 32' $S1_{Bx}$, while the projected length 36' of vector 1' in the frontal plane is calculated as $$d_{S1F} = \sqrt{(A_z-B_z)^2+(A_x-B_x)^2}$$

and horizontal vector angle 37' relative to the axis z is calculated by using the function $$\tan S1\alpha_F = \frac{AB_{S1x}}{AB_{S1z}}.$$

Coordinates 31', 34' of initial point $S1_A$ and coordinates 33', 35' of terminal point $S1_B$ of vector 1' in the sagittal plane are $A_{S1}(A_y;A_z)$ and $B_{S1}(B_y;B_z)$. Coordinates 31',34',33',35' of vector 1' are therefore $AB_{S1}(B_y-A_y;B_z-A_z)$. The projected length 36' of vector 1' in the sagittal plane is calculated as $$d_{S1S} = \sqrt{(A_z-B_z)^2+(A_y-B_y)^2}$$

and sagittal vector angle 37' relative to the axis y is calculated by using the function $$\tan S1\alpha_S = \frac{AB_{S1z}}{AB_{S1y}}.$$

Coordinates 30', 31' of initial point $S1_A$ and coordinates 32', 33' of terminal point $S1_B$ of vector 1' in the horizontal plane are $S1_A(A_x;A_y)$ and $S1_B(B_x;B_y)$. Coordinates of vector 1' are therefore $A B_{S1}(B_x-A_x;B_y-A_y)$. The lateral translation (also called lateral ejection [23,24]) from the axis y is again equal to the value of coordinate 32' $S1_{Bx}$ while the projected length 36' of vector 1' in the horizontal plane is calculated as $$d_{S1H} = \sqrt{(A_y-B_y)^2+(A_x-B_x)^2}$$

and horizontal vector angle 37' relative to the axis y is calculated by using the function $$\tan S1\alpha_H = \frac{AB_{S1x}}{AB_{S1y}}.$$

Thus, combined values for each vertebra vector 1' containing its 3D parameters in the frontal, sagittal and horizontal plane are to be presented as vector point coordinates $A_{S1}(A_x;A_y;A_z)$ and $B_{S1}(B_x;B_y;B_z)$, 3D vector coordinates $AB_{S1}(X;Y;Z)$ and vector angles $S1\alpha_F$, $S1\alpha_S$, and $S1\alpha_H$, respectively.

Definition of Pelvis Vectors Based on Sacrum Vector S1

The pelvis is also represented by a pair of vectors for both sides, left vector PL-S1 and right vector PR-S1, and are used for obtaining data about position, orientation, symmetry, asymmetry, deformation, rotation and torsion of the pelvis.

The pelvis vectors are based on and originate of the sacrum vector described above. They are placed inside the same coordinate system used for the vertebra vectors and they are illustrated in FIG. 8A-C.

Initial point A's of vector PL-S1 and vector PR-S1 is identically located at the midpoint 16' of sacrum vector 1'. Pelvis vector lines are connected with the left acetabular center 12' for vector PL-S1 (17') and the right acetabular center 13' for vector PR-S1 (18'), respectively. Thus, terminal point B's of pelvis vectors PL-S1 and PR-S1 (19' and 20') are identical to the left and right acetabular centers.

Calculation of Parameters for Pelvis Vectors Based on Sacrum Vector S1

FIGS. 9A-C display elements of pelvis vectors that are used for vector parameter calculations.

Coordinates 38',42' of initial point PL-S1$_A$ and coordinates 40', 43' of terminal point PL-S1$_B$ of vector 17' in the frontal plane are $A_{PL-S1}(A_x;A_z)$ and $B_{PL-S1}(B_x;B_z)$. Coordinates 38', 42',40',43' of vector $AB_{PL-S1}$ are therefore $AB_{PL-S1}(B_x-A_x; B_z-A_z)$. The projected length 44' of vector 17' in the frontal plane is calculated as $$d_{PL-S1F} = \sqrt{(A_z-B_z)^2+(A_x-B_z)^2}$$

and horizontal vector angle 45' relative to the axis z is calculated by using the function $$\tan PL-S1\alpha_F = \frac{AB_{PL-S1x}}{AB_{PL-S1z}}.$$

Coordinates 46',50' of initial point PR-S1$_A$ and coordinates 48',51' of terminal point PR-S1$_B$ of vector 18' in the frontal plane are $A_{PR-S1}(A_x;A_z)$ and $B_{PR-S1}(B_x;B_z)$. Coordinates 46', 50',48',51' of vector $AB_{PR-S1}$ are therefore $AB_{PR-S1}(B_x-A_x; B_z-A_z)$. The projected length 52' of vector 18' in the frontal plane is calculated as $$d_{PR-S1F} = \sqrt{(A_z-B_z)^2+(A_x-B_z)^2}$$

and horizontal vector angle 53' relative to the axis z is calculated by using the function $$\tan PR-S1\alpha_F = \frac{AB_{PR-S1x}}{AB_{PR-S1z}}.$$

Coordinates 39', 43' of initial point PL-S1$_A$ and coordinates 41', 50' of terminal point PL-S1$_B$ of vector 17' in the sagittal plane are $A_{PL-S1}(A_y;A_z)$ and $B_{PL-S1}(B_y;B_z)$. Coordinates 39', 43',41',50' of vector 17' are therefore $AB_{PL-S1}(B_y-A_y;B_z-A_z)$. The projected length 44' of vector 17' in the sagittal plane is calculated as $$d_{PL-S1S} = \sqrt{(A_z-B_z)^2+(A_y-B_y)^2}$$

and sagittal vector angle 45' relative to the axis y is calculated by using the function $$\tan PL-S1\alpha_S = \frac{AB_{PL-S1z}}{AB_{PL-S1y}}.$$

Coordinates 47', 51' of initial point PR-S1$_A$ and coordinates 49', 50' of terminal point PR-S1$_B$ of vector 18' in the sagittal plane are $A_{PR-S1}(A_y;A_z)$ and $B_{PRL-S1}(B_y;B_z)$. Coordinates 47', 51',49',50' of vector 18' are therefore $AB_{PR-S1}(B_y-A_y;B_z-A_z)$. The projected length 52' of vector 18' in the sagittal plane is calculated as $$d_{PR-S1S} = \sqrt{(A_z-B_z)^2+(A_y-B_y)^2}$$

and sagittal vector angle 53' relative to the axis y is calculated by using the function $$\tan PR-S1\alpha_S = \frac{AB_{PR-S1z}}{AB_{PR-S1y}}.$$

Coordinates 30', 31' of initial point PL-S1$_A$ and coordinates 32', 33' of terminal point PL-S1$_B$ of vector 17' in the horizontal plane are PL-S1$_A(A_x;A_y)$ and PL-S1$_B(B_x;B_y)$. Coordinates 30',31',32',33' of vector 17' are therefore $AB_{PL-S1}(B_x-A_x;B_y-A_y)$. The projected length 44' of vector 17' in the horizontal plane is calculated as $$d_{PL-S1H} = \sqrt{(A_y-B_y)^2+(A_x-B_x)^2}$$

and horizontal vector angle 45' relative to the axis y is calculated by using the function $$\tan PL-S1\alpha_H = \frac{AB_{PL-S1x}}{AB_{PL-S1y}}.$$

Thus, combined values for each vertebra vector 17' containing its 3D parameters in the frontal, sagittal and horizontal plane are to be presented as vector point coordinates $A_{PL-S1}(A_x;A_y;A_x)$ and $B_{PL-S1}(B_x;B_y;B_z)$, 3D vector coordinates $AB_{PL-S1}(X;Y;Z)$ and vector angles PL-S1$\alpha_F$, PL-S1$\alpha_S$, and PL-S1$\alpha_B$, respectively.

Coordinates 46', 47' of initial point PR-S1$_A$ and coordinates 48', 49' of terminal point PR-S1$_B$ of vector 18' in the horizontal plane are PR-S1$_A(A_x;A_y)$ and PR-S1$_B(B_x;B_y)$. Coordinates 46',47',48',49' of vector 18' are therefore $AB_{PR-S1}(B_x-A_x;B_y-A_y)$. The projected length 52' of vector 18' in the horizontal plane is calculated as $$d_{PR-S1H} = \sqrt{(A_y-B_y)^2+(A_x-B_x)^2}$$

and horizontal vector angle 53' relative to the axis y is calculated by using the function $$\tan PR-S1\alpha_H = \frac{AB_{PR-S1x}}{AB_{PR-S1y}}.$$

Thus, combined values for each vertebra vector 18' containing its 3D parameters in the frontal, sagittal and horizontal plane are to be presented as vector point coordinates $A_{PR-S1}(A_x;A_y;A_z)$ and $B_{PR-S1}(B_x;B_y;B_z)$, 3D vector coordinates $AB_{PR-S1}(X;Y;Z)$ and vector angles PR-S1$\alpha_F$, PR-S1$\alpha_S$, and PR-S1$\alpha_B$, respectively.

Sacrum Plateau Vector Definition

Current methods for characterization of pelvic position and orientation, especially in the sagittal plane based on lateral radiographs, are based on the determination of the contour line corresponding to the sacrum plateau, which is the most proximal part of the pelvis, representing the upper endplate of vertebra S1. With respect to compatibility with current concepts and measurement methods we also provide the concept and system in this application an alternative for the sacrum vector, vector S1, described above. This is done with the introduction of sacrum plateau vector, vector SP, and illustrated in FIG. 11A-C.

Initial point $A_{SP}$ (22') for vector SP (21') is the midpoint of the spinal canal (29') at the level of the sacrum plateau 7', as shown in FIG. 11B and FIG. 11C, respectively. Vector SP line is drawn according to the sacrum plateau line 8' in sagittal plane. Terminal point $B_{SP}$ (23') is the point where the sacrum plateau ends in sagittal plane projection.

Calculation of Sacrum Plateau Vector Parameters

All principles for the calculation of vector SP parameters are identical with aforementioned methods for calculating vector parameters for vector S1. Except for labels of items used inside, the identical nature for these calculations warrants no further descriptions and illustrations here.

Definition of Pelvis Vectors Based on Sacrum Plateau Vector SP

Similarly to the sacrum vector-based pelvis vectors, the pelvis may also be represented by a similar pair of vectors for both sides, left vector PL-SP and right vector PR-SP, and to be used for obtaining data about position, orientation, symmetry, asymmetry, deformation, rotation and torsion of the pelvis. This kind of method may be more closely related to procedures available in the art and therefore more acceptable for those familiar with the art itself. We provide this as an alternative solution to the same problem and no preference is put on either method. Both could be used for obtaining valid data for the same purposes, namely, generating data about position, orientation, symmetry, asymmetry, deformation, rotation and torsion of the pelvis.

The pelvis vector SP's are based on and originate of the sacrum plateau vector described above. They are placed inside the same coordinate system used for the vertebra vectors and they are illustrated in FIG. 12A-C.

Initial point A's of vector PL-SP and vector PR-SP is identically located at the midpoint 24' of sacrum plateau vector 21'. Pelvis vector SP lines are connected with the left acetabular center 12' for vector PL-SP (25') and the right acetabular center 13' for vector PR-S1 (26'), respectively. Thus, terminal point B's of pelvis vectors PL-SP and PR-SP (27' and 28') are identical to the left and right acetabular centers 12' and 13'.

Calculation of Parameters for Pelvis Vectors Based on Sacrum Plateau Vector SP

All principles for the calculation of vector PL-SP and PR-SP parameters are identical with aforementioned methods for calculating vector parameters for vectors PL-S1 and PR-S1, respectively. Except for labels of items used inside, the identical nature for these calculations warrants no further descriptions and illustrations here.

Measurement of Pelvic Parameters by Sacrum Vector S1 and Pelvis Vectors Based on Sacrum Vector S1

Position and orientation of pelvis is currently characterized by sagittal and frontal plane pelvic parameters as described by publications earlier [26,27]. Sagittal balance, hence, full balance of the upper body is influenced by these parameters, therefore, knowledge and measurement of these parameters are very important for a total, especially a three-dimensional, evaluation of the spinal column. Sagittal pelvic parameters are: pelvic tilt (or pelvic version), sacral slope and pelvic incidence. The former two are dependent upon body position, hence, called positional pelvic parameters, while the latter one, pelvic incidence, is an anatomically constant, morphologic parameter, its value being shown to be independent of positional changes.

Pelvic version is defined by (1) the line through the midpoint of the sacral plate and midpoint of the femoral heads axis, and (2) a vertical line. Sacral slope is defined as the angle between the sacral plate and a horizontal line. Pelvic incidence is defined as the angle between the line perpendicular to the sacral plate at its midpoint and the line connecting this point to the axis of the femoral heads. It is an anatomical parameter, unique to each individual, independent of the spatial orientation of the pelvis. Pelvic incidence is also to be noted as the algebraic sum of sacral slope and pelvic tilt.

Lateral pelvic obliquity, or by a shorter form, pelvic obliquity, is a frontal plane term characterizing a tilted pelvic position due to any underlying cause, i.e., pelvic deformation, discrepancy in lower limb length.

Measurement of these important pelvic parameters based on the sacrum vector S1 and its related pelvis vectors PL-S1 and PR-S1 are illustrated in FIG. 10A-B.

Sacral slope 55' (SS) is measured based on calculating vector S1 coordinates $A_{S1}(A_y;A_z)$ and $B_{S1}(B_y;B_z)$ as shown above. Coordinates of vector S1 are therefore $AB_{S1}(B_y-A_y; B_z-A_z)$. Sacral slope is equal to the angle between vector S1 and axis y in the sagittal plane, therefore it is calculated by the function $$\tan SS = \frac{AB_{S1z}}{AB_{S1y}}.$$

In normal individuals with symmetrical pelvis the pelvis vectors PL-S1 and PL-S1 are aligned together and projected on each other in sagittal plane. Pelvic version 56' (PV) is measured based on calculating vector either vector PL-S1 or PR-S1 coordinates. We demonstrate here calculations by using vector PL-S1 coordinates, $A_{PL-S1}(A_y;A_z)$ and $B_{PL-S1}(B_y;B_z)$ as shown above. Coordinates of vector PL-S1 are therefore $AB_{PL-S1}(B_y-A_y;B_z-A_z)$. Pelvic version is equal to the angle between vector PL-S1 and axis z in the sagittal plane, therefore PV is calculated by the function $$\tan PV = \frac{AB_{PL-S1y}}{AB_{PL-S1z}}.$$

Pelvic incidence 54' (PI) is equal to the algebraic sum of the value of PV and SS, hence

PI=PV+SS.

Pelvic obliquity 57' (PO) is not present in normal cases. To determine whether pelvic obliquity is present, one would evaluate the equation $$\tan PL - S1\alpha_S = \tan PR - S1\alpha_S \text{ or}$$

$$\frac{AB_{PL-S1z}}{AB_{PL-S1y}} = \frac{AB_{PR-S1z}}{AB_{PR-S1y}}.$$

When the equation returns false, there is a pelvic asymmetry present that results in lateral pelvic obliquity. PO could then be calculated by following simple trigonometry rules.

Three-Dimensional Visualization of the Scoliotic Spine in the Thoracic and Lumbar Region with Vertebra Vectors Complemented with Sacrum Vector and Pelvic Vectors Visualization of the scoliotic spine showing a double major curve (Lenke type 6CN [1]) is illustrated in FIGS. 13A-C. Vertebra vectors $T_1$-$L_V$ of the thoracic and lumbar region with sacrum vector S1 and corresponding pelvis vectors PL-S1 and PR-S1, respectively, are shown in FIG. 13A in the frontal plane, in FIG. 13B in the sagittal plane, and FIG. 13C in the horizontal plane. For easier differentiation of vertebrae from one another, especially in the horizontal plane, a color-coded key shown in Legend of FIG. 13A-B-C is used.

Some novelties and benefits of the new system and method of vertebra vectors and visualization, characterization and numerical description of spinal deformities based on vertebra vectors are the following:

- This is the first method for the concurrent visualization, characterization and parametric evaluation of all important characteristics of scoliotic vertebrae in a spinal deformation: vertebral size, position, orientation and spatial rotation are all described by vertebra vector parameters
- Of special interest are the ability to view the vertebrae of the thoracic and lumbar region from above in the horizontal plane: no routine clinical device or method has been available to carry this out for scoliotic patients.
- Conventional angulation measurement methods to describe and characterize the spinal column in the frontal and sagittal plane are preserved and readily applicable by vertebra vectors as well.
- A simplified and easy-to-understand interpretation of digital images and 3D reconstructions provided by any of the current radiodiagnostic devices is promoted by vertebra vectors.
- Vertebra vectors provide a simplification of the very complex visual information in digital images and 3D reconstructions provided by current radiodiagnostic devices, without sacrificing any of the information important to understand underlying processes in spinal deformation: 3D data on vertebral size, position, orientation and rotation.
- The magnitude of the vector is determined by the vertebral body size, accurately modelling the size changes of vertebrae from the upper thoracic to the lumbar region.
- Positioning of the vertebra vector inside the vertebral body neutralizes the variance in axial rotation due to vertebral body torsion since the relative vertical distance of the vector from the upper endplate is constant for each vertebra [20], therefore, a vertebra vector defined in this way is least prone to be affected by scoliotic vertebral shape changes.
- Coordinates of vertebra vectors can be determined in a coordinate system based on the interacetabular axis (x), the sagittal median axis (y) and the axis (z) perpendicular to the intersection of the axes x and y, providing a mathematical description of the position, orientation and rotation of each vertebra vector.
- Since the axis y of the coordinate system used by this method corresponds to the sagittal median axis of the body and a vertebra vector corresponds to the vertebral axis in the horizontal plane, vector angle $\alpha_H$ relative to the axis y is identical to the vertebral axial rotation in the horizontal plane.
- Vertebral axial rotation can therefore be determined directly through the use of vertebra vectors, without involving any of the known auxiliary or 3D reconstruction-based methods [5-11, 20-22].
- In light of the individual variations in the metrics of the spino-pelvic skeletal system, it is very important to have a calibrated scale for this coordinate system that allows the direct interindividual comparison of values and can form a basis for classification.
- The calibration method used with vertebra vectors employs an individually specific, relative calibration scale.
- Applicable on spatially calibrated stereoradiography images or 3D reconstructions of current radiodiagnostic devices, after registration of landmarks required to determine a vertebra vector.

Future applications and benefits based on or arising from the use of the new system and method of vertebra vectors and visualization, characterization and numerical description of spinal deformities employing vertebra vectors are the following:

- Vertebra vector provide visual and numerical information in all three planes, based on mathematical formulae ready to be used in built-in software algorithms.
- May be used directly or indirectly by any of the current radiodiagnostic devices and their clinical diagnostic systems.
- Vertebra vectors may be useful in the analysis of the pathomechanism of spinal deformities.
- Vertebra vectors may significantly affect or fundamentally change the basic understanding of processes in the surgical treatment.
- Could be the basis for and may influence therapeutic strategies for surgical correction in 3D.
- May be useful in the evaluation of surgical correction in 3D.
- Could be the basis for 3D modelling of procedures during surgical correction.
- Might serve as the basis for the creation of a truly 3D classification of scoliosis.
- Could be useful in mathematical or biomechanical applications, with theoretical or practical purposes, for 3D characterization and 3D modelling of the spinal column.
- Could serve as a basic groundwork for quantitative evaluation and modelling of biomechanical loads and forces of the spinal column in 3D.
- The sacrum and pelvis vectors complement and complete the system introduced by vertebra vectors, allowing a more accurate full characterization in 3D.
- With sacrum and pelvis vectors, currently used pelvic parameters are easily calculated together with vertebra vector-based calculations for the spinal geometry.
- The coordinate system implemented for vertebra vectors is based on an individual scale which makes it possible to present individually valid data while providing a basis for inter-individual comparisons.
- The coordinate system is further enhanced and its use is further augmented by the introduction of sacrum and pelvis vectors, by providing a built-in possibility of accommodating pelvic tilting, asymmetry or deformations, due to any causes, all that could present problems with the validity of coordinate data inside the coordinate system; evaluation of pelvic symmetry could result in the appropriate modification of the coordinate value for each vertebra, providing a truly and individually valid dataset.
- Furthermore, the combination of the pelvis-based augmentation of the coordinate system and extension of the system distally to the ground, element of the lower limbs are also easily characterized inside the same Cartesian system
- The extension of the coordinate system may open the possibility to present and characterize lower limb components as vectors themselves, again, in an individually valid 3D parameters.
- The extension of the coordinate system may open even further possibilities to present and characterize the skull, cervical spine region, shoulders, rib cage etc. with individually valid 3D parameters.

By implementing body surface sensors or markers, the system may be useful in live, online evaluation of 3D pelvic parameters in software navigation systems.

With its complementation with pelvis vectors and extension of the individual 3D reference coordinate system, evaluation of results of corrective procedures—conservative and surgical alike—could be carried out by the implementation of body surface markers or sensors and linking with 3D-aware systems for biomechanical measurements.

The system and concept may be used for existing or newly developed software navigation systems for lower limb endoprothesis surgery, providing an individually valid 3D reference system intraoperatively.

REFERENCES

1. Lenke L G, Betz R R, Harms J et al. Adolescent Idiopathic Scoliosis A New Classification to Determine Extent of Spinal Arthrodesis. J Bone Joint Surg Am. 2001; 83-A: 1169-1181.
2. Nash, C., Moe, J. A study of vertebral rotation. J. Bone Joint Surg 1969; 51A:223.
3. Perdriolle R. La scoliose. Maloine S. A. ed., Paris 1969.
4. Perdriolle R, Vidal J. Morphology of scoliosis: three-dimensional evolution. Orthopaedics 1987; 10:909-915.
5. Mehta M H. Radiographic estimation of vertebral rotation in scoliosis. J Bone Joint Surg Br 1973; 55Br: 513-520.
6. Omeroglu H, Ozekin O, Bicimoglu A. Measurement of vertebral rotation in idiopathic scoliosis using the Perdriolle torsiometer: a clinical study on intraobserver and interobserver error. Eur. Spine J 1996; 5:167-171.
7. Richards B S. Measurement error in assessment of vertebral rotation using the Perdriolle torsiometer. Spine 1992; 17:513-517.
8. Aaro S, Dahlborn M. Estimation of vertebral rotation and spine rib cage deformity in scoliosis by computer tomography. Spine 1981; 6:460-467.
9. Ho E K W, Upadlyay S S, Chan F L et al. New method of measuring vertebral rotation from computed tomographic scans. Spine 1993; 18:1173-1177.
10. Krismer M, Chen A M, Steinlecher M et al. Measurement of vertebral rotation: a comparison of two methods based on CT scans. J Spinal Disord 1999; 12:126-130.
11. Gocen S, Aksu M G, Baktiroglu L et al. Evaluation of computer tomographic methods to measure vertebral rotation in adolescent idiopathic scoliosis: an intraobserver and interobserver analysis. J Spinal Disord 1998; 11:210-214.
12. Stokes I A F. Three-dimensional terminology of spinal deformity. A report presented to Scoliosis Research Society by the Scoliosis Research Society Working Group on 3-D terminology of spinal deformity. Spine 1994; 19:236-248.
13. Sangole A P, Aubin C-E, Labelle H et al.: Three-Dimensional Classification of Thoracic Scoliotic Curves. Spine 2009; 34:91-99.
14. Nobel Prize in Physics 1992, http://nobelprize.org/nobel_prizes/physics/laureates/1992/index.html
15. Kalifa G, Charpak G, Maccia C et al. Evaluation of a new low-dose digital x-ray device: first dosimertric and clinical result in children. Pediatr Radiol 1998; 28:557-561.
16. Dubousset J. Charpak G, Dorion I et al. Le system EOS. Nouvelle Imagerie Osteo-Articulaire basse dose en position debout. E-mémoire de l'Academie National de Chirugie 2005; 4:22-27.
17. Dubousset J. Charpak G, Dorion I et al. A new 2D and 3D imaging approach to musculosceletal physiology and pathology with low-dose radiation and the standing position: the EOS system. Bull Acad Natl Med 2005; 189:287-297.
18. Le Bras A, Laporte S, Mitton D et al. 3D detailed reconstruction of vertebrae with low dose digital stereoradiography. Stud Health Technol Inform 2002; 91:286-290.
19. Le Bras A, Laporte S, Mitton D et al. A biplanar reconstruction method based on 2D and 3D contours: application to the distal femur. Comput Methods Biomech Biomed Engin 2003; 6:1-6.
20. Roaf R. Rotation movements of the spine with special reference to scoliosis. J Bone Joint Surg Br 1958; 40:312-332.
21. Skalli W, Lavaste F, Descrimes J L. Quantification of three-dimensional vertebral rotations in scoliosis: what are the true values? Spine 1995; 20:546-553.
22. Yazici M, Acaroglu E R, Alanay A et al. Measurement of vertebral rotation in standing versus supine position in adolescent idiopathic scoliosis. J Pediatr Orthop 2001; 21:252-256.
23. Dubousset J. Three-Dimensional Analysis of the Scoliotic Deformity. In: The Pediatric Spine: Principles and Practice. Ed: Weinstein S L., Raven Press Ltd., New York, pp:479-496, 1994.
24. Dubousset J. Biomechanics of the Spine During Growth. In: Biomechanics and Biomaterials in Orthopedics. Ed: Poitout D G., Springer-Verlag London Ltd., pp: 257-281, 2004.
25. Cobb J. Outline for the study of scoliosis. Am Acad Orthop Surg Instr Course Lect 1948; 5:261-275.
26. Legaye J, Duval-Beaupere G, Hecquet J, Marty C. *Pelvic incidence: a fundamental pelvic parameter for three-dimensional regulation of spinal sagittal curves*. Eur Spine J. 1998; 7(2):99-103.
27. Boulay C, Tardieu C, Hecquet J, Benaim C et al. Sagittal alignment of spine and pelvis regulated by pelvic incidence: standard values and prediction of lordosis. Eur Spine J. 2006; 4:415-422.

LIST OF REFERENCE SIGNS

1—vertebra vector AB
2—right pedicle of the vertebra
3—left pedicle of the vertebra
4—rigth pedicular centroid (PCR)
5—left pedicular centroid (PCL)
6—interpedicular line ($IP_{PC}$)
7—initial point A of the vertebra vector
8—symmetry axis of the upper endplate of the vertebral body
9—line parallel to the symmetry axis of the upper endplate of the vertebral body
10—terminal point B of the vertebra vector
11—ventral contour line of the vertebral body
12—right acetabular center of the pelvis
13—left acetabular center of the pelvis
14—origo of the coordinate system
15—coordinate point $A_x$
16—coordinate point $A_z$
17—coordinate point $B_x$
18—coordinate point $B_z$
19—frontal plane vector angle $\alpha_F$
20—projected vector size in the frontal plane, $d_{ABF}$
21—coordinate point $A_y$
22—coordinate point $B_y$
23—sagittal plane vector angle $\alpha_S$
24—projected vector size in the sagittal plane, $d_{ABS}$
25—horizontal plane vector angle $\alpha_H$ 26—projected vector size in the horizontal plane, $d_{ABH}$
27—interpedicular line with right-to-left direction, interpedicular vector IPR
28—coordinate point $PCR_x$
29—coordinate point $PCR_z$
30—coordinate point $PCL_x$
31—coordinate point $PCL_z$
32—frontal plane interpedicular $\alpha_{IPR}$ angle relative to axis x
33—interpedicular line with left-to-right direction, interpedicular vector IPL
34—frontal plane interpedicular $\alpha_{IPL}$ angle relative to axis x
1'—vertebra vector S1, sacrum vector, vector S1
2'—pelvis
3'—first sacral vertebra, vertebra S1
4'—left and right pedicular centroids of vertebra S1
5'—interpedicular midpoint, initial point $A_{S1}$ of sacrum vector
6'—vector line of sacrum vector
7'—upper endplate of vertebra S1, sacrum plateau
8'—sacrum plateau line, parallel with sacrum vector line
9'—terminal point $B_{S1}$ of sacrum vector
10'—left acetabulum
11'—right acetabulum
12'—left acetabular centroid
13'—right acetabular centroid
14'—interacetabular line
15'—interacetabular midpoint, origo of the coordinate system for vertebra vectors
16'—midpoint of vector S1, initial point A of pelvis vector left and right, point $A_{PL/PR}$
17'—vector S1-based pelvis vector left, vector PL-S1
18'—vector S1-based pelvis vector right, vector PR-S1
19'—terminal point $B_{PL-S}1$ of vector PL-S1, left acetabular centroid
20'—terminal point $B_{PR-S1}$ of vector PR-S1, right acetabular centroid
21'—sacrum plateau vector, vector SP
22'—initial point $A_{SP}$ of vector SP
23'—terminal point $B_{SP}$ of vector SP
24'—midpoint of vector SP, initial point A of pelvis vector left and right, point $A_{PL/PR}$
25'—vector SP-based pelvis vector left, vector PL-SP
26'—vector SP-based pelvis vector right, vector PR-SP
27'—terminal point $B_{PL-SP}$ of vector PL-SP, left acetabular centroid
28'—terminal point $B_{PR-SP}$ of vector PR-SP, right acetabular centroid
29'—spinal canal at sacrum plateau level
30'—vector S1 initial point A coordinate X, $S1_{Ax}$
31'—vector S1 initial point A coordinate Y, $S1_{Ay}$
32'—vector S1 terminal point B coordinate X, $S1_{Bx}$
33'—vector S1 terminal point B coordinate Y, $S1_{By}$
34'—vector S1 initial point A coordinate Z, $S1_{Az}$
35'—vector S1 terminal point B coordinate Z, $S1_{Bz}$
36'—vector S1 length, $d_{S1}$
37'—vector S1 angle $\alpha$, S1$\alpha$
38'—vector PL-S1 initial point A coordinate X, PL-S1$_{Ax}$
39'—vector PL-S1 initial point A coordinate Y, PL-S1$_{Ay}$
40'—vector PL-S1 terminal point B coordinate X, PL-S1$_{Bx}$
41'—vector PL-S1 terminal point B coordinate Y, PL-S1$_{By}$
42'—vector PL-S1 initial point A coordinate Z, PL-S1$_{Az}$
43'—vector PL-S1 terminal point B coordinate Z, PL-S1$_{Bz}$
44'—vector PL-S1 length, $d_{PL-S1}$
45'—vector PL-S1 angle $\alpha$, PL-S1$\alpha$
46'—vector PR-S1 initial point A coordinate X, PR-S1$_{Ax}$
47'—vector PR-S1 initial point A coordinate Y, PR-S1$_{Ay}$
48'—vector PR-S1 terminal point B coordinate X, PRS1$_{Bx}$
49'—vector PR-S1 terminal point B coordinate Y, PR-S1$_{By}$
50'—vector PR-S1 initial point A coordinate Z, PR-S1$_{Az}$
51'—vector PR-S1 terminal point B coordinate Z, PR-S1$_{Bz}$
52'—vector PR-S1 length, $d_{PR-S}1$
53'—vector PR-S1 angle $\alpha$, PR-S1$\alpha$
54'—pelvic incidence, PI
55'—sacral slope, SS
56'—pelvic tilt, pelvic version, PV
57'—lateral pelvic obliquity, PO

The invention claimed is:

1. A method for multi-dimensional visualization of a spinal column/spinal deformities comprising the steps of
obtaining an image of a spinal column definitely showing each vertebral body in the spinal column;
analyzing each vertebral body and defining mathematical/geometrical characteristic parameters uniquely characterizing respective vertebrae;
preparing vectors comprising an initial point (7) and a terminal point (10) according to the characteristic parameters, wherein the initial point (7) is constituted by a midpoint of a line connecting two pedicular centroids (4, 5) of the vertebral body and terminal point (10) as an intersection of a ventral surface contour (11) of a vertebral body and a line (9) originating from the initial point (7) drawn in a horizontal symmetry axis (8) of the vertebral body while contained in a plane parallel to the plane determined by an upper endplate of the vertebral body;
defining a three-dimensional coordinate system with an axis x formed by an interacetabular line connecting two acetabular centers (12, 13) of a pelvis in horizontal plane, with an axis y being the line perpendicular to a frontal plane and the interacetabular line and with an axis z being perpendicular to a horizontal plane and the axis x at an origin (14) of the coordinate system;
scaling and calibrating the coordinate system based on the length of the interacetabular line in the horizontal plane view;
determining coordinates of initial point (7) and terminal point (10), respectively of each vector in all three planes and placing the prepared vectors inside of the coordinate system;
determining coordinates of the left and right pedicular centroids (4, 5) of each vertebra in the frontal plane;
taking interpedicular line (IPPC) as an interpedicular vector and choosing the initial point determining the direction of the interpedicular vector as the pedicular centroid more distant from the axis x;
calculating coordinates of the interpedicular vector;
determining a coordinate system for positioning the vertebra vectors by the position of the two acetabular centers of the pelvis;
defining a sacrum vector and calculating sacrum vector parameters;
defining pelvis vectors based on a predetermined sacrum vector;
calculating parameters for the pelvis vectors based on the predetermined sacrum vector;
defining a sacrum plateau vector and calculating sacrum plateau vector parameters;
defining pelvis vectors based on a predetermined sacrum plateau vector;
calculating parameters for the pelvis vectors based on the predetermined sacrum plateau vector;
measuring pelvic parameters by said sacrum vector and pelvis vectors based on said sacrum vector;

visualizing the spine in a three-dimensional manner in the thoracic and lumbar region with said vertebra vectors complemented with sacrum vector and pelvic vectors.

2. The method of claim 1 wherein obtaining an image of a spinal column comprises producing two-dimensional radiographs of a spinal column.

3. The method of claim 2 wherein producing two-dimensional radiographs of a spinal column comprises aquiring radiographs of a spinal column of a patient being in a standing posture.

4. A system for multi-dimensional visualization of a spinal column/spinal deformities comprising an image of a spinal column definitely showing each vertebral body in the spinal column;

characteristic parameters uniquely characterizing respective vertebrae;

vectors comprising an initial point (7) and a terminal point (10) according to the characteristic parameters, wherein the initial point (7) is constituted by a midpoint of a line connecting two pedicular centroids (4, 5) of the vertebral body and terminal point (10) as an intersection of a ventral surface contour (11) of a vertebral body and a line (9) originating from the initial point (7) drawn in a horizontal symmetry axis (8) of the vertebral body while contained in a plane parallel to the plane determined by an upper endplate of the vertebral body;

a three-dimensional coordinate system with an axis x formed by an interacetabular line connecting two acetabular centers (12, 13) of a pelvis in horizontal plane, with an axis y being the line perpendicular to a frontal plane and the interacetabular line and with an axis z being perpendicular to a horizontal plane and the axis x at an origin (14) of the coordinate system;

a calibrated the coordinate system based on the length of the interacetabular line in the horizontal plane view;

coordinates of initial point (7) and terminal point (10), respectively of each vector in all three planes and placing the prepared vectors inside of the coordinate system;

coordinates of the left and right pedicular centroids (4, 5) of each vertebra in the frontal plane;

an interpedicular line (IPPC) as an interpedicular vector and choosing the initial point determining the direction of the interpedicular vector as the pedicular centroid more distant from the axis x;

coordinates of the interpedicular vector;

a coordinate system for positioning the vertebra vectors by the position of the two acetabular centers of the pelvis;

a sacrum vector and calculating sacrum vector parameters;

pelvis vectors based on a predetermined sacrum vector;

parameters for the pelvis vectors based on the predetermined sacrum vector;

a sacrum plateau vector and calculating sacrum plateau vector parameters;

pelvis vectors based on a predetermined sacrum plateau vector;

parameters for the pelvis vectors based on the predetermined sacrum plateau vector;

pelvic parameters and pelvis vectors measured based on said sacrum vector;

visualization of the spine in a three-dimensional manner in the thoracic and lumbar region with said vertebra vectors complemented with sacrum vector and pelvic vectors.

* * * * *